United States Patent [19]

Sano et al.

[11] Patent Number: 4,554,289
[45] Date of Patent: Nov. 19, 1985

[54] OF4949

[75] Inventors: Susumu Sano; Katsushige Ikai, both of Muko; Hiroyuki Kuroda, Shiga; Teruya Nakamura, Kusatsu; Hiroshi Enomoto, Nagaokakyo; Yoji Ezure, Otsu, all of Japan

[73] Assignees: Takara Shuzo Co., Ltd.; Nippon Shinyaku Co., Ltd., both of Japan

[21] Appl. No.: 564,923

[22] Filed: Dec. 23, 1983

[30] Foreign Application Priority Data

Dec. 25, 1982 [JP] Japan .................. 57-234640
Nov. 2, 1983 [JP] Japan .................. 58-206169
Nov. 11, 1983 [JP] Japan .................. 58-212926

[51] Int. Cl.[4] .................. A61K 31/395; C07D 273/08; C12P 17/14
[52] U.S. Cl. .................. 514/450; 260/239.3 T; 435/120
[58] Field of Search .................. 260/239.3 T; 424/244

[56] References Cited

U.S. PATENT DOCUMENTS 4,371,533 2/1983 Akimoto et al. ............. 260/239.3 T

Primary Examiner—Robert T. Bond
Attorney, Agent, or Firm—Jacobs & Jacobs

[57] ABSTRACT

Compounds of the formula (I):

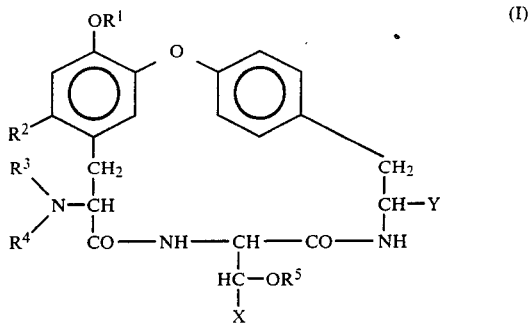

and pharmaceutically acceptable salts thereof wherein $R^1$ is hydrogen, alkyl of 1 to 10 carbon atoms or acyl of 1 to 6 carbon atoms; $R^2$ is hydrogen or halo; $R^3$ is hydrogen, alkyl of 1 to 6 carbon atoms or acyl of 1 to 6 carbon atoms; $R^4$ is hydrogen or alkyl of 1 to 6 carbon atoms; $R^5$ is hydrogen or acyl of 1 to 6 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 10 carbon atoms or benzyl are useful for inhibiting the activity of amino-peptidase B, exhibit immunomodulating action against living organisms and exhibit anti-inflammatory activity.

21 Claims, 8 Drawing Figures

OF4949

The present invention relates to novel compounds including a substance named OF4949, to processes for the production thereof, to pharmaceutical compositions containing such compounds as the active agent and to methods of treatment utilizing said compounds.

More particular, the compounds of the present invention are represented by the formula:

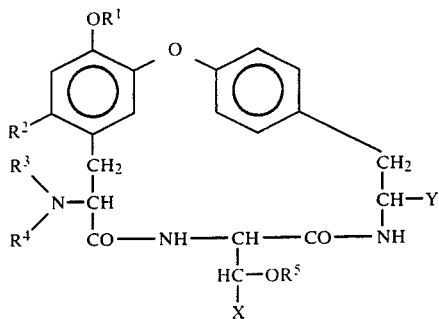

or a pharmaceutically acceptable salt thereof wherein $R^1$ is hydrogen, alkyl of 1 to 10 carbon atoms or acyl of 1 to 6 carbon atoms; $R^2$ is hydrogen or halo; $R^3$ is hydrogen, alkyl of 1 to 6 carbon atoms or acyl of 1 to 6 carbon atoms; $R^4$ is hydrogen or alkyl of 1 to 6 carbon atoms; $R^5$ is hydrogen or acyl of 1 to 6 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 10 carbon atoms or benzyl.

According to one embodiment of the present invention, $R^1$ is hydrogen, alkyl of 1 to 4 carbon atoms or acyl of 1 to 4 carbon atoms; $R^2$ is hydrogen, fluoro, chloro or bromo; $R^3$ is hydrogen, alkyl of 1 to 4 carbon atoms or acyl of 1 to 4 carbon atoms; $R^4$ is hydrogen or alkyl of 1 to 4 carbon atoms; $R^5$ is hydrogen or acyl of 1 to 4 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 4 carbon atoms or benzyl.

According to a further embodiment of the present invention, $R^1$ is hydrogen or alkyl of 1 or 2 carbon atoms; $R^2$ is hydrogen, fluoro, chloro or bromo; $R^3$ is hydrogen or alkyl of 1 or 2 carbon atoms; $R^4$ is hydrogen or alkyl of 1 or 2 carbon atoms; $R^5$ is hydrogen or acyl of 1 or 2 carbon atoms; X is $CONH_2$, hydroxyalkyl of 1 or 2 carbon atoms or $COOR^6$ wherein $R^6$ is hydrogen or alkyl of 1 or 2 carbon atoms; and Y is $CONH_2$, hydroxyalkyl of 1 or 2 carbon atoms or $COOR^7$ wherein $R^7$ is hydrogen or alkyl of 1 or 2 carbon atoms.

According to a further embodiment of the present invention, the compound is of the formula (II):

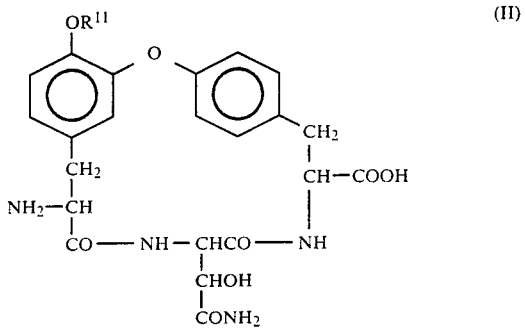

wherein $R^{11}$ is hydrogen or methyl.

Two particularly useful compounds according to the present invention are those of the formula (III):

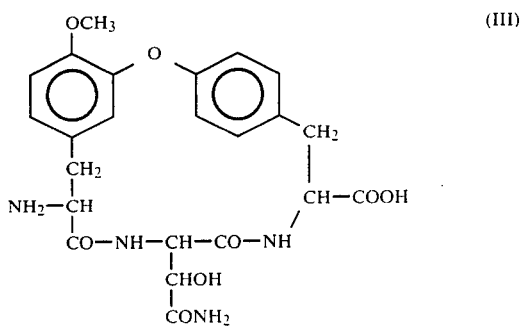

named OF4949-I which is a compound of the formulaa (II) wherein $R^{11}$ is methyl and the compound of the formula (IV):

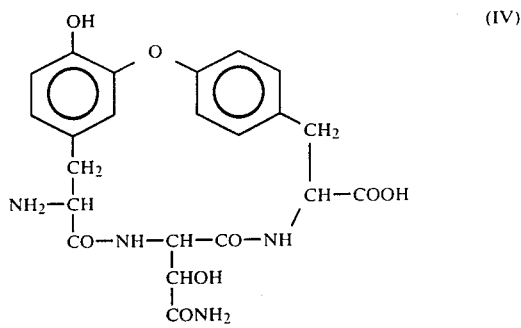

named OF4949-II which is a compound of the formula (II) wherein $R^{11}$ is hydrogen.

The compounds of the present invention and their pharmaceutically acceptable salts have been found to be useful for inhibiting the activity of amino-peptidase B, to exhibit immunomodulating action against living organisms and to exhibit anti-inflammatory action inhibiting the bradykinin formation.

The immunomodulating action which the compounds of the present invention exhibit makes these compounds useful in the treatment of diseases such as autoimmune diseases, i.e. nephritis, rheumatic arthritis, generalized lupus erythematodes and the like, as well as malignant tumors. It is known in the art, for example, that levamisole has been reported to be somewhat effective as an immunotherapeutic agent for cancer and is useful in the treatment of rheumatic arthritis.

Various immunomodulating agents have been produced heretofore. However, the agents heretofore developed exhibit contraindications when administered for prolong periods of time and up to the present time, satisfactory immunomodulating agents without side effects have not been produced.

It has also been discovered that the compounds of the present invention markedly potentiate the cellular immunity when tested by using delayed hypersensitivity caused by inoculation of erythrocytes of sheep as an antigen injected in the hind paws of mice.

The compounds of the present invention are water-soluble amphoteric substances of the peptide type, some of which have been originally produced from micro-organisms belonging to the genus Penicillium isolated from soil samples.

Soil samples of micro-organisms of the genus Penicillium have been isolated from soil samples in the Kyoto Prefecture, Japan and their mycological properties are as follows:

(1) State of growth on various culture media (24° C., two weeks).

1. Malt extract agar.

The growth is slow and the diameter of colonies 2.0 to 2.5 cm in two weeks. Surfaces of colonies are dark green to bluish green colour. Centres of the colonies are somewhat rising. Surroundings of the colonies are flat and form velvet-like mycelia. Edges of the colonies are with 1 to 2 mm width and are white. Some parts of the reverse side are yellow but no pigment production to agar is observed.

2. Potato-glucose agar.

The growth is slow and the diameter of colonies 2.5 to 3.0 cm in two weeks. Centres of the colonies are white to greyish green. Surroundings are yellow to yellowish green and form velvet-like mycelia. On the surfaces of the colonies, there are radiated canals. The reverse sides are pale yellow to yellowish orange, with slight fimbria, and do not produce pigment into agar.

3. Czapek's agar.

The growth is very slow and appearance and growth of conidia are also no good. Diameters of colonies 1.5 to 2.0 cm in two weeks. On the surfaces, pale yellow to yellowish orange and velvet-like mycelia are produced. They are sometimes white to grey in some parts. Reverse sides are not coloured and do not produce pigment into agar.

4. Czapek's agar added Corn steepliquor.

The growth is slow and the diameters of the colonies 2.0 to 2.5 cm in two weeks. On the surface, yellowish green to dark green and velvet-like mycelia are produced. Centres of the colonizes may sometimes form fimbria. Edges of the colonies are 1 to 2 mm width and are white. Reverse sides are not coloured and do not produce pigment into agar.

5. Malt juice agar.

The growth is good and the diameters of the colonies reach to 3.0 to 4.0 cm in two weeks. Centres of the colonies are somewhat risen and velvet-like in dark green to bluish green colour. Surroundings are yellow to yellowish green. Both surfaces and back side form many fimbria. Reverse sides are in yellowish orange to yellowish brown colour and do not produce pigment into agar.

(2) Morphological data.

Mycelia are colourless and septate. Most of penicillus are biverticillately symmetric though monoverticillately symmetric in some cases. Conidia are elliptical—3.0 to 4.0 $\mu$m in length and 2.5 to 3.0 $\mu$m in width. Size of chains of the conidia is 50 to 80 $\mu$m. Sterigmata are lanceolate with acuminate tips and are produced in groups, about four to eight, in parallel. The length is 10.0 to 13.0 $\mu$m and the width is 2.0 to 2.5 $\mu$m. Metulae are in groups, about two to eight, in condensed or somewhat diversified state. The length is 10 to 13 $\mu$m and the width is 2.5 to 3.0 $\mu$m. Conidiophore are 50 to 80 $\mu$m in length and 2.5 to 3.0 $\mu$m in width. Many of them do not come out from aerial mycelia or from vegetative mycelia but exert though some of them come out from mycelia.

(3) Conditions for growth.

pH: Growth observed within a pH range of 2 to 12 and the optimum pH for growth is 3 to 6.

Temperature: Growth is possible within a temperature range of 6° to 33° C. and the optimum range is 18° to 28° C.

The characteristics of the micro-organism set forth above identifies it as *Pencillium rugulosum*. Mycological properties of *P. rugulosum* are disclosed in detail in "A Manual of the Penicillia" by Raper and Thom (Hafner, 1968), "Fungi in Agricultural Soils" by Domsh and Gams (Longman, 1972) and *Journal of General and Applied Microbiology*, volume 2, page 1, 1956 by Abe.

*Penicillium rugulosum* has been deposited at the Fermentation Research Institute, Agency of Industrial Science and Technology, Ministry of International Trade and Industry of Japan under the deposit number FERM BP-203.

In addition to the specific culture deposited which is intended to be a representative one, all micro-organisms belonging to the genus Penicillium can be used to produce the compounds of the present invention. Furthermore, natural and artificial mutants thereof, for example those produced by irradiation with ultraviolet light or by treatment with mutation inducers for micro-organisms such as nitrosoguanidine are also useful for producing the compounds of the present invention.

In culturing the micro-organisms referred to above, the medium used may be liquid or solid and in general shake culture or aerated culture with stirring using liquid media has been found to be suitable. All of the usual kinds of media known in the art are useful for promoting the growth of the fungi for producing the compounds of the present invention. Thus, as a carbon source, carbohydrates such as, for example, glucose, fructose, maltose, sucrose, lactose, dextrin, starch, glycerol, sorbitol and the like and vegetable oils and fats such as, for example, soybean oil can be used. Examples of nitrogen sources applicable are peptone, yeast extract, meat extract, soybean powder, cotton seed powder, corn steep liquor, malt extract, amino acids such as glutamic acid, aspartic acid, tyrosine, phenylalanine and the like and salts thereof, urea, ammonium salts, nitrates and so forth. In addition, micro-nutrients such as inorganic salts such as magnesium phosphate, salts of potassium, sodium, calcium, iron, manganese and the like and vitamins such as vitamin $B_1$, calcium pantothenate and the like may also be added thereto to an adequate extent.

When it is desired to perform the culture in large quantities, it is generally desirable to culture in a liquid.

Culture conditions such as pH of the medium, the culture temperature and the like can be varied as is well known in the fermentation art. However, in a liquid shake culture or aerated culture with stirring using a liquid medium, the pH may preferably be from 4 to 7.

The culturing temperature should be from 25° to 30° C. and the culturing period should preferably be from 2 to about 10 days.

Substances according to the present invention are present both in the culture filtrate and in the mycelia and can be separated from either or both. In separating the desired substances from the culture filtrate or the mycelia, various means conventionally used in separating and purifying organic substances from cultures of micro-organisms can be used depending upon the properties of the particular compound. Useful, for example, are absorption chromatography using activated charcoal or non-ionic adsorbing resin, ion exchange chromatography using ion exchangers, partition chromatography using cellulose and the like, and reversed phase partition chromatography using silica gel combined with alkyl groups.

More particularly, the culture filtrate, aqueous acetone extract of mycelia or a solution containing the present invention substances is passed through a column filled with activated charcoal (e.g., manufacture of Wako Pure Chemicals), Diaion HP-20 (Mitsubishi Chem Ind), etc. and the adsorbed substances are eluted with acid, alkali, water, methyl alcohol, ethyl alcohol, and/or acetone. The eluate is then passed through a column filled with Dowex 50W (H+ type; Dow Chemical) and other strongly acidic cation exchanger or with Dowex 1x2 (OH− type; Dow Chemical) and other strongly basic anion exchanger and the adsorbed substances are eluted with acid, alkali or a solution of salt.

It is also possible to remove impurities by passing the solution passed through Dowex 1x2 (Cl type). The resulting solution is treated with Diaion HP-20 or others as described before to adsorb the desired substances, after which it is eluted with a solvent to desalt, and concentrated in vacuo to afford the desired product in yellowish brown colour. This crude product is subjected to a treatment with a column of crystalline cellulose Avicel (Funakoshi Co), LiChroprep (silica gel combined with alkyl groups; Waters Co) or others and then developed with acid, alkali, water, buffer, methyl alcohol, acetonitrile, propyl alcohol, n-butyl alcohol and/or the like to afford a single product.

Physical and chemical properties of those substances are as follows:

(1) Molecular formulae: OF4949-I, $C_{23}H_{26}O_8N_4$. OF4949-II, $C_{22}H_{24}O_8N_4$.

(2) Elementary analyses: OF4949-I calculated as $C_{23}H_{26}O_8N_4.2H_2O$: C 52.30, H 5.46, N 10.64; Found: C 52.87, H 5.79, N 10.72%, OF4949-II calculated as $C_{22}H_{24}O_8N_4.2H_2O$: C 51.60, H 5.48, N 11.06; Found: C 51.97, H 5.55, N 11.02%.

(3) Molecular weights: Molecular weights measured by SIMS (secondary ion mass spectrometry) are 486 for OF4949-I and 472 for OF4949-II.

(4) Melting points: Both OF4949-I and OF4949-II melt at around 280° C. with decomposition.

(5) Specific rotatory power: OF4949-I: $[\alpha]_D^{25} = -64.8°$ (c=1.0, water). OF4949-II: $[\alpha]_D^{25} = -42.6°$ (c=1.0, water).

(6) Ultraviolet absorption spectra: Wavelengths and $E_{1\ cm}^{1\%}$ values showing maximum absorptions when OF4949-I and OF4949-II are dissolved in the following solvents are as shown in Table 1.

TABLE 1

| | unit: $\lambda_{max}$ nm ($E_{1cm}^{1\%}$) | |
|---|---|---|
| Solvents | OF4949-I | OF4949-II |
| Water | 213,(304), 230 (shoulder 236) 273(46), 283 (shoulder 40) | 214(282), 272(57), 279 (58) |
| 0.05 N—HCl | 212(302), 228(shoulder 227) 273(46), 283(shoulder 40) | 213(279), 272(56), 279 (57) |
| 0.5 N—NaOH | 214(308), 273 (47) 283 (shoulder 40) | 218(313), 242(shoulder 175), 297 (68) |

(7) Infrared absorption spectra: Wavelengths showing maximum absorptions measured with potassium bromide tablets of OF4949-I and OF4949-II are as given in Table 2.

TABLE 2

| Unit: $cm^{-1}$ | |
|---|---|
| OF4949-I | OF4949-II |
| 3400, 1650, 1580, 1500, 1380, 1260, 1225, 1160, 1120, 1100, 1020 | 3400, 1650, 1580, 1500, 1430, 1380, 1270, 1250, 1225, 1160, 1120 |

(8) Solubilities: Both OF4949-I and OF494-II are soluble in water, alkaline water, and dimethyl sulfoxide; hardly soluble in methyl alcohol and ethyl alcohol; and insoluble in n-propyl alcohol, n-butyl alcohol, acetone, ethyl acetate, chloroform, ether, benzene, and hexane.

(9) Colour reactions: Both OF4949-I and OF4949-II are positive to ninhydrin reaction, potassium permanganate reaction, Rydon-Smith reaction, and iodine reaction; negative to Sakaguchi reaction, Prochazka reaction, Hanes reaction, and anthrone reaction. OF4949-II is positive to $FeCl_3$ reaction.

(10) Neutral, acidic or basic properties: Both OF4949-I and OF4949-II are amphoteric substances.

(11) Thin layer chromatography: $R_f$ values on silica gel plates (Merck) are as given in Table 3.

TABLE 3

| | $R_f$ values | |
|---|---|---|
| Solvents | OF4949-I | OF4949-II |
| n-Butyl alcohol, acetic acid and water (3:1:1) | 0.32 | 0.32 |
| n-Butyl alcohol, pyridine, acetic acid, and water (3:4:3:1) | 0.35 | 0.35 |
| n-Propyl alcohol and 28% ammonia water (2:1) | 0.41 | 0.32 |
| Ethyl alcohol and 28% ammonia water (2:1) | 0.54 | 0.48 |

(12) High-performance liquid chromatography: Retention volumes and times of OF4949-I and of OF4949-II using Nucleosil $5C_{18}$ (Macherey-Nagel Co) are as given in Table 4.

TABLE 4

| | OF4949-I | OF4949-II |
|---|---|---|
| Retention Time | 9.9 minutes | 4.2 minutes |
| Retention Volume | 5.0 ml | 2.1 ml |
| Size of the column | ⌀ 4.0 mm × 150.0 mm | |
| Filler | Nucleosil $5C_{18}$ | |
| Solvent | 0.1 M citrate buffer (pH 5.7) and acetonitrile (90:10) | |
| Liquid speed | 0.5 ml/minute | |
| Identification | UV 275 nm | |

(13) Colours of the substances: Both OF4949-I and OF4949-II are colourless powder.

(14) Proton nuclear magnetic resonance spectra: Chemical shifts, proton numbers and multiplicities of OF4949-I and OF4949-II measured in heavy ammonia water are as follows:
Unit: Chemical shift (ppm).
Internal standard: DSS.

OF4949-I: 2.66 (1H, t), 2.75–3.00 (2H, m), 3.37 (1H, dd), 3.70 (1H, dd), 3.93 (3H, s), 4.42 (1H, d), 4.48 (1H, dd), 5.83 (1H, d), 6.87 (2H, m), 7.07 (2H, m), 7.26 (1H, dd), 7.46 (1H, dd).

OF4949-II: 2.65 (1H, t), 2.70–2.95 (2H, m), 3.36 (1H, dd), 3.67 (1H, dd), 4.40 (1H, d), 4.46 (1H,dd), 5.78 (1H, d), 6.67 (1H,d), 6.85 (1H,dd), 7.05 (1H, dd), 7.22 (1H, dd), 7.41 (1H, dd).

(15) $^{13}$C nuclear resonance spectra: Chemical shifts of OF4949-I and OF4949-II measured in 0.06N heavy ammonia water are as fofllows:

Unit: Chemical shift (ppm).
Internal standard: p-dioxane (67.4 ppm).

OF4949-I: 178.7, 176.0, 174.9, 168.3, 153.4, 149.4, 148.0, 136.5, 132.9, 131.5, 128.2, 125.0, 123.1, 122.1, 116.2, 113.0, 72.9, 57.9, 56.7, 55.1, 53.8, 39.7, 38.9

OF4949-II: 178.8, 176.0, 175.8, 168.3, 154.1, 149.0, 145.6, 136.1, 132.8, 131.4, 127.3, 125.2, 123.1, 122.0, 117.0, 116.8, 73.0, 57.9, 55.1, 54.0, 39.7, 39.1

OF4949-I and OF4949-II are similar substances having similar properties. They have the same structure except that OF4949-II has one phenolic hydroxyl group while OF4949-I has a methoxy in place of the hydroxyl group.

The present invention includes salts, particularly pharmaceutically acceptable salts with metals, organic bases, mineral acids and organic acids. Structure of representative compounds of the present invention are set forth in Table 5; infrared absorption spectra and proton NMR spectra are set forth in Table 6.

TABLE 5

[Structure (I) of the compound shown]

| Compound Number | $R^1$ | $R^2$ | $R^3$ | $R^4$ | $R^5$ | X | Y |
|---|---|---|---|---|---|---|---|
| 1 | H | H | H | H | H | $CONH_2$ | $COOCH_3$ |
| 2 | H | H | H | H | H | COOH | COOH |
| 3 | H | H | H | H | H | $COOCH_3$ | $COOCH_3$ |
| 4 | H | H | H | H | H | $CONH_2$ | $CH_2OH$ |
| 5 | H | H | H | H | H | $CH_2OH$ | $CH_2OH$ |
| 6 | H | H | CHO | H | H | $CONH_2$ | COOH |
| 7 | H | H | CHO | H | H | $CONH_2$ | $COOCH_3$ |
| 8 | H | H | $COCH_3$ | H | H | $CONH_2$ | COOH |
| 9 | H | H | $COCH_3$ | H | H | $CONH_2$ | $COOCH_3$ |
| 10 | H | H | $CH_3$ | $CH_3$ | H | $CONH_2$ | COOH |
| 11 | H | H | $C_2H_5$ | H | H | $CONH_2$ | COOH |
| 12 | H | H | $C_2H_5$ | $C_2H_5$ | H | $CONH_2$ | COOH |
| 13(OF4949-I) | $CH_3$ | H | H | H | H | $CONH_2$ | COOH |
| 14 | $CH_3$ | H | H | H | H | $CONH_2$ | $COOCH_3$ |
| 15 | $CH_3$ | H | H | H | H | $CONH_2$ | $COOC_4H_9$ |
| 16 | $CH_3$ | H | H | H | H | $CONH_2$ | $COOCH_2C_6H_5$ |
| 17 | $CH_3$ | H | H | H | H | $CONH_2$ | $CONH_2$ |
| 18 | $CH_3$ | H | H | H | H | COOH | COOH |
| 19 | $CH_3$ | H | H | H | H | $COOCH_3$ | $COOCH_3$ |
| 20 | $CH_3$ | H | H | H | H | COOH | $CONH_2$ |
| 21 | $CH_3$ | H | H | H | H | $CH_2OH$ | $CH_2OH$ |
| 22 | $CH_3$ | H | CHO | H | H | $CONH_2$ | COOH |
| 23 | $CH_3$ | H | CHO | H | H | $CONH_2$ | $COOCH_3$ |
| 24 | $CH_3$ | H | CHO | H | H | $CONH_2$ | $COOC_4H_9$ |
| 25 | $CH_3$ | H | $COCH_3$ | H | H | $CONH_2$ | COOH |
| 26 | $CH_3$ | H | $COCH_3$ | H | H | $CONH_2$ | $COOCH_3$ |
| 27 | $CH_3$ | H | $COCH_3$ | H | $COCH_3$ | $CONH_2$ | $COOCH_3$ |
| 28 | $CH_3$ | H | $C_2H_5$ | H | H | $CONH_2$ | COOH |
| 29 | $CH_3$ | Br | H | H | H | $CONH_2$ | COOH |
| 30 | $CH_3$ | Br | H | H | H | COOH | COOH |
| 31 | $C_4H_9$ | H | H | H | H | $CONH_2$ | COOH |
| 32 | $COCH_3$ | H | H | H | $COCH_3$ | $CONH_2$ | COOH |

TABLE 6

| Compd No. | Infrared Absorption Spectra (cm$^{-1}$) | Proton Nuclear Magnetic Resonance Spectra (δ values) |
|---|---|---|
| 1 | 3400, 1730, 1670, 1500, | 3.70 ($OCH_3$), 392 (CH), 4.58 (CH), |

TABLE 6-continued

| Compd No. | Infrared Absorption Spectra (cm$^{-1}$) | Proton Nuclear Magnetic Resonance Spectra (δ values) |
|---|---|---|
| | 1430, 1275, 1225, 1110 | 4.67 (CH), 5.85 (CH), 6.5-7.4 (CH × 6) |
| 2 | 3350, 1630, 1590, 1500, 1395, 1230, 1115, 960 | 2.5-3.0 (CH$_2$), 3.34, 3.62 (CH$_2$), 4.16 (CH), 4.48 (CH), 5.75 (CH), 6.5-7.5 (CH × 6) |
| 3 | 3400, 1735, 1650, 1500, 1430, 1270, 1225, 1120 | 3.56 (OCH$_3$), 4.05 (CH), 4.5-4.8 (CH × 2), 5.81 (CH), 6.1-7.4 (CH × 6) |
| 4 | 3400, 1640, 1270, 1225, 1110 | 3.71 (CH$_2$), 4.16 (CH), 5.80 (CH), 6.6-7.5 (CH × 6) |
| 5 | 3400, 1640, 1590, 1500, 1270, 1225, 1110 | 3.45 (CH$_2$), 3.56 (CH$_2$), 4.34 (CH), 5.77 (CH), 6.6-7.5 (CH × 6) |
| 6 | 3400, 1720, 1660, 1500, 1380, 1270, 1225, 1110 | 4.30 (CH), 5.95 (CH), 6.5-7.5 (CH × 6), 8.10 (CHO) |
| 7 | 3450, 1735, 1670, 1500, 1430, 1275, 1230, 1110 | 3.72 (OCH$_3$), 3.95 (CH), 5.80 (CH), 6.2-7.4 (CH × 6), 7.94 (CHO) |
| 8 | 3400, 1720, 1660, 1505, 1430, 1275, 1225, 1110 | 1.97 (CH$_3$CO), 4.30 (CH), 5.98 (CH), 6.4-7.6 (CH × 6) |
| 9 | 3400, 1735, 1670, 1505, 1430, 1275, 1225, 1110 | 1.95 (CH$_3$CO), 4.25 (CH), 5.92 (CH), 6.4-7.5 (CH × 6) |
| 10 | 3400, 1670, 1590, 1505, 1390, 1220, 1115 | 2.52 (CH$_3$ × 2), 4.25 (CH), 6.30 (CH), 6.5-7.5 (CH × 6) |
| 11 | 3350, 1660, 1580, 1500, 1390, 1250, 1220, 1120 | 1.20 (CH$_3$), 3.90 (CH), 4.32 (CH), 5.98 (CH), 6.7-7.6 (CH × 6) |
| 12 | 3400, 1650, 1590, 1500, 1390, 1225, 1120 | 1.06 (CH$_3$ 2), 4.27 (CH), 6.40 (CH), 6.6-7.5 (CH × 6) |
| 13 | 3400, 1660, 1580, 1500, 1380, 1260, 1225, 1120, 1020 | 2.6-3.0 (CH$_3$), 3.38, 3.70 (CH$_2$), 3.93 (OCH$_3$), 4.42 (CH), 5.82 (CH), 6.8-7.5 (CH × 6) |
| 14 | 3400, 1740, 1680, 1510, 1270, 1240, 1130, 1020 | 3.70 (OCH$_3$), 3.80 (OCH$_3$), 3.93 (CH), 4.60 (CH), 4.67 (CH), 5.86 (CH), 6.6-7.4 (CH × 6) |
| 15 | 3400, 1735, 1670, 1500, 1265, 1235, 1130, 1020 | 0.97 (CH$_3$), 3.86 (OCH$_3$), 4.80 (CH), 5.92 (CH), 6.7-7.5 (CH × 6) |
| 16 | 3400, 1740, 1650, 1500, 1265, 1230, 1160, 1120 | 3.87 (OCH$_3$), 5.22 (CH$_2$), 5.98 (CH), 6.5-7.5 (CH × 6), 7.41 (5H) |
| 17 | 3400, 1670, 1510, 1270, 1235, 1130, 1020 | 3.78 (OCH$_3$), 5.77 (CH), 6.5-8.1 (CH × 6, CONH$_2$ × 2, CONH × 2) |
| 18 | 3400, 1720, 1660, 1500, 1265, 1235, 1130, 1020 | 3.83 (OCH$_3$), 4.56 (CH), 4.66 (CH), 5.82 (CH), 6.6-7.4 (CH × 6) |
| 19 | 3400, 1730, 1650, 1500, 1430, 1260, 1225, 1125, 1020 | 3.72 (OCH$_3$), 3.80 (OCH$_3$), 3.88 (OCH$_3$), 4.34 (CH), 6.7-7.4 (CH × 6) |
| 20 | 3400, 1650, 1600, 1500, 1265, 1230, 1120, 1020 | 3.79 (OCH$_3$), 4.24 (CH × 2), 6.54 (CH), 6.9-7.1 (CH × 6), 7.17, 7.35 (CONH$_2$) |
| 21 | 3400, 1650, 1505, 1260, 1230, 1130, 1020 | 3.4-3.6 (CH$_2$), 3.6-3.8 (CH$_2$), 3.94 (OCH$_3$). 4.53 (CH), 5.81 (CH), 6.8-7.5 (CH × 6) |
| 22 | 3400, 1720, 1680, 1645, 1505, 1270, 1230, 1130 | 3.84 (OCH$_3$), 4.43 (CH), 5.85 (CH), 6.5-7.6 (CH × 6), 8.07 (CHO) |
| 23 | 3400, 1740, 1640, 1500, 1265, 1230, 1125, 1020 | 3.72 (OCH$_3$), 3.80 (OCH$_3$), 4.00 (CH), 5.78 (CH), 6.4-7.5 (CH × 6), 7.95 (CHO) |
| 24 | 3350, 2950, 1735, 1680, 1500, 1265, 1235, 1130, 1030 | 0.8-1.1 (CH$_3$), 3.76 (OCH$_3$), 5.92 (CH), 6.5-7.5 (CH × 6), 8.04 (CHO) |
| 25 | 3350, 1730, 1670, 1500, 1265, 1230, 1130, 1020 | 1.99 (CH$_3$CO), 3.87 (OCH$_3$), 4.30 (CH), 5.90 (CH), 6.5-7.5 (CH × 6) |
| 26 | 3400, 1740, 1660, 1500, 1435, 1265, 1235, 1130 | 1.99 (CH$_3$CO), 3.78 (OCH$_3$), 3.84 (OCH$_3$), 4.23 (CH), 5.88 (CH), 6.5-7.5 (CH × 6) |
| 27 | 3350, 1730, 1650, 1500, 1425, 1360, 1260, 1220, 1120, 1020 | 1.82 (CH$_3$CO), 2.07 (CH$_3$CO), 3.70 (OCH$_3$), 3.78 (OCH$_3$), 5.78 (CH), 6.4-7.4 (CH × 6) |
| 28 | 3300, 1680, 1590, 1510, 1390, 1265, 1235, 1130, 1020 | 0.9-1.3 (CH$_3$), 4.14 (CH), 4.70 (CH), 5.88 (CH), 6.5-7.5 (CH × 6) |
| 29 | 3400, 1670, 1600, 1500, 1385, 1260, 1225, 1145 | 3.91 (OCH$_3$), 4.21 (CH), 5.96 (CH), 6.8-7.5 (CH × 5) |
| 30 | 3400, 1630, 1495, 1390, 1220, 1170, 1145, 1020 | 3.87 (OCH$_3$), 4.42 (CH), 5.94 (CH), 6.7-7.5 (CH × 5) |
| 31 | 3400, 1660, 1505, 1390, 1260, 1235, 1130 | 1.96 (CH$_3$), 1.4-1.8 (CH$_2$ × 2), 4.04 (CH$_2$), 4.18 (CH), 4.66 (CH), 5.82 (CH), 6.6-7.4 (CH × 6) |
| 32 | 3400, 1740, 1680, 1500, 1370, 1265, 1210, 1115 | 2.18 (CH$_3$CO), 2.35 (CH$_3$CO), 4.95 (CH), 6.0 (CH), 6.7-7.6 (CH × 6) |

Compounds of the present invention other than OF4949-I and OF4949-II can be produced from those two compounds by the following procedures or combinations thereof.

Compounds of the formula (I) wherein R$^1$ is lower alkyl can be produced by alkylating a compound of the formula (I) wherein R$^1$ is hydrogen. Alkylation is a procedure well known in the art and this procedure may be considered the application of known alkylation procedures. Examples of suitable alkylating agents are alkyl halides, alkyl sulfates, alkyl p-toluenesulfonates or diazoparaffins or alcohols in the presence of acid catalysts or dehydrating agents such as N,N'-dicyclohexylcarbodiimide. The reaction conditions would vary depending upon the specific materials used and would be well within the skill of one working in the art familiar with alkylation procedures. In some cases, the reaction may advantageously include the addition of a base. For example, in alkylating with an alkyl halide, methyl halide and butyl halide are used in the production of compounds wherein methyl and butyl would be the alkyl group desired for $R^1$. In these reactions, solvents such as dimethyl sulfoxide, N,N-dimethylformamide, 1,2-dimethoxyethane, tetrahydrofuran and the like would be used and bases such as sodium amide, potassium carbonate, triethylamine, sodium hydroxide, barium hydroxide, silver oxide, sodium hydride and the like would also be used.

The reaction temperature would generally be from room temperature to about 60° C. Room temperature is preferred. The reaction time, of course, will vary according to the materials used, but in most cases the reaction would be completed within 50 minutes to fifty hours. The reaction time and its dependency upon the reactants used would be well appreciated by one skilled in the art.

After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds according to the present invention wherein $R^1$ is lower acyl can be produced by acylating a compound of the formula (I) wherein $R^1$ is hydrogen. Again, the acylation procedure is per se well known and one skilled in the art would be fully capable of conducting such an acylation procedure being fully aware of the time, temperature and solvents to be selected. Suitable acylation procedures include the use of carboxylic acid in the presence of dehydrating agents such as N,N'-dicyclohexylcarbodiimide, the reaction with acid halides in the presence of bases such as pyridine, dimethylaniline, tetramethylurea, metal magnesium and the like and the reaction with acid anhydrides in the presence of catalysts such as sulfuric acid, p-toluenesulfonic acid, zinc chloride, sodium acetate and pyridine.

As an example of the variance of reaction conditions, when the compound to be produced is one wherein $R^1$ is acyl, it may be conveniently produced by the use of acetic anhydride in the presence of catalysts such as sulfuric acid, p-toluenesulfonic acid, zinc chloride, sodium acetate or pyridine. The reaction temperature will generally be in the range of from about 0° to about 60° C., preferably room temperature. The reaction time will generally be within the range of fifty minutes to fifty hours. The reaction time and its dependency upon the reactants used would be well appreciate by one skilled in the art.

After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein $R^2$ is halo can be produced by the known technique of halogenation of a compound of the formula (I) wherein $R^2$ is hydrogen. The halogenation procedure is per se well known and one skilled in the art would be fully capable of conducting such a halogenation procedure being fully aware of the time, temperature and solvents to be selected. Suitable halogenation procedures include the reaction with halogen in the presence of catalysts such as iron, Lewis acids, iodine and the like, the reaction with halogenating agents such as N-bromosuccinic imide, oxalyl chloride, sulfuryl chloride, tertiary butyl hyopchlorite, tertiary butyl hyopbromite and the like. The reaction time and its dependency upon the reactants used would be well appreciated by one skilled in the art. For example, when the compound to be produced is one wherein $R^2$ is bromo, such may be produced by halogenating with N-bromosuccinimide in a polar solvent such as water, alcohol and the like. The reaction temperature would generally be from about 0° C. to about 80° C., preferably room temperature. The reaction time will generally be within the range of fifty minutes to fifty hours. The reaction time and its dependency upon the reactants used would be well appreciated by one skilled in the art. After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein $R^3$ is lower acyl can be produced from a compound of the formula (I) wherein $R^3$ is hydrogen by acylating the amino group. Examples of acylation procedures include condensation with carboxylic acid using a condensation agent such as carbodiimides, silicone tetrachloride anhydrous pyridine, titanium chloride and the like, reaction with acid halides in the presence of bases such as tertiary amines, sodium hydroxide, sodium acetate, alkali carbonates, pyridine and the like and the reaction with acid anhydride in the presence of reaction accelerators if necessary, such as sulfuric acid or sodium acetate. The reaction time and its dependency upon the reactants used would be well appreciated by one skilled in the art. For example, when the compound to be produced is one wherein $R^3$ is formyl, they are obtained by reacting formic acid-acetic anhydride and those in which an acetyl group is present in $R^3$ are obtained by a reaction with acetic anhydride-water, acetic anhydride-methyl alcohol, acetic anhydride-pyridine, acetic anhydride-sodium acetate and the like. The reaction temperature will generally be in the range of from about −20° to about 120° C. The reaction time will generally be within the range of five minutes to fifty hours. The reaction time and its dependency upon the reactants used would be well appreciated by one skilled in the art. After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein $R^3$ and/or $R^4$ are lower alkyl can be produced from a compound of the formula (I) wherein $R^3$ and $R^4$ are both hydrogen by known alkylation procedures. Examples of suitable alkylation procedures are the reaction with alkyl halides, alkyl sulfates such as dimethyl sulfate or alkyl sulfonates, reductive alkylation using aldehydes and the like. The reaction time will generally be within the range of five minutes to fifty hours. The reaction time and its dependency upon the reactants used would be well appreciated by one skilled in the art. Compounds in which either $R^3$ or $R^4$ is lower alkyl are produced by control of the amount of alkylating agent, reaction temperature and reaction time. Thus, by careful control of these conditions, compounds of the formula (I) wherein either $R^3$ or $R^4$ or both is lower alkyl may be produced as desired.

In the reductive alkylation for the production of N-methyl, N-ethyl and the like, it is preferred to use aqueous solutions of aldehydes such as formaline or acetaldehyde and then to reduce the intermediates with lithium aluminum hydride, sodium cyanoborohydride, sodium borohydride or the like. Particularly suitable as a reducing agent is sodium cyanoborohydride. Examples of suitable solvents are water, alcohol and acetonitrile. The reaction temperature will generally be in the range of from about 0° to about 60° C., preferably room temperature. The reaction time and its dependency upon the reactants used would be well appreciated by one skilled in the art. As the reaction time becomes longer, the compound in which one of $R^3$ and $R^4$ is lower alkyl is first produced and then changed to a compound in which both $R^3$ and $R^4$ are lower alkyl moieties. Accordingly, the reaction can be stopped when an adequate amount of the desired product is produced. After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein $R^5$ is lower acyl can be produced by known acylation techniques from a compound of the formula (I) wherein $R^5$ is hydrogen. An example of suitable acylation procedures are reaction with acid halides in the presence of catalysts such as pyridine, dimethylaniline, tetramethylurea, magnesium metal and other bases; reaction with acid anhydrides in the presence of catalysts such as sulfuric acid, p-toluenesulfonic acid, zinc chloride, sodium acetate and pyridine. The acylation procedure is per se well known and one skilled in the art would be fully capable of conducting such an acylation procedure being fully aware of the time, temperature and solvents to be selected.

Compounds of the formula (I) wherein $R^5$ is acetyl can be produced by the reaction with acetic anhydride-sulfuric acid, acetic anhydride-p-toluene sulfonic acid or acetic anhydride-pyridine. Acetic acid anydride and pyridine are most preferred. The reaction temperature will generally be in the range of from about 0° to about 100° C., preferably room temperature to 60° C. The reaction time will generally be within the range of fifty minutes to fifty hours. The reaction time and its dependency upon the reactants used would be well appreciated by one skilled in the art.

After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein X is carboxylic acid can be produced from compounds of the formula (I) wherein X is a carboxylic acid amide by converting carboxylic acid amides to carboxylic acids. Examples include hydrolysis with an acid or an alkali, hydrolysis with sodium peroxide, nitrosoation with an acid amide followed by conversion into carboxylic acid. Suitable nitrosoating agents are nitrites, alkyl nitrites, nitrosyl chloride, nitrogen dioxide and the like. This procedure is per se well known and one skilled in the art would be fully capable of conducting such a procedure being fully aware of the time, temperature and solvents to be selected. For example, when X is a carboxylic acid amide and Y is carboxylic acid, heating in hydrochloric acid at 50° to 100° C. for fifty minutes to fifty hours, preferably at about 100° C. for two to eight hours in 2N hydrochloric acid produces a compound of the formula (I) in which both X and Y are carboxylic acid.

After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein wherein X is a carboxylic acid ester can be produced from compounds of the formula (I) in which X is a carboxylic acid by esterification procedures per se known in the art. Examples include dehydration reaction with an alcohol using a catalyst such as a mineral acid, i.e. sulfuric acid, hydrochloric acid, etc., an organic acid, i.e. an aromatic sulfonic acid and the like, a Lewis acid, i.e. boron fluoride etherate and the like, a cation exchange resin, reacting with an O-alkylating agent such as a diazomethane or reacting with a dialkyl sulfate or with an alkyl halide. This procedure is per se well known in the art and one skilled in the art would be fully capable of conducting such a procedure being fully aware of the time, temperature and solvents to be selected. For example, when X is a carboxylic acid methyl ester, compounds of the formula (I) can be produced by treating a corresponding carboxylic acid in methyl alcohol with a catalyst such as a mineral acid, for example sulfuric acid or hydrochloric acid, an organic acid such as aromatic sulfonic acid, a Lewis acid such as a boron fluoride etherate, a cation exchange resin, and the like. The reaction temperature will generally be in the range of from about 0° to about 60° C., preferably room temperature. The reaction time will generally be within the range of fifty minutes to fifty hours. The reaction time and its dependency upon the reactants used would be well appreciated by one skilled in the art. After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein X is $CH_2OH$ are produced by reducing a compound of the formula (I) wherein X is a carboxylic acid ester with a suitable reducing agent which does not affect groups other than the carboxylic acid ester group. Suitable reducing agents are alkoxy lithium aluminum hydride, sodium borohydride, lithium borohydride, sodium borohydride-aluminum chloride, lithium bromide, diborane and the like, preferably lithium borohydride. This reduction procedure is per se well known in the art and one skilled in the art would be fully capable of conducting such a reduction procedure being fully aware of the time, temperature and solvents to be selected. Suitable solvents are ethyl ether, tetrahydrofuran and dioxane. The reaction temperature will generally be in the range of from 0° C. to the boiling point of the solvent. The reaction time will generally be within the range of fifty minutes to fifty hours. The reaction time and its dependency upon the reactants used would be well appreciated by one skilled in the art.

After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein Y is a carboxylic acid ester are produced by treating a compound of formula (I) in which Y is a carboxylic acid with a known esterifying agent. Examples of esterification are dehydration reaction with an alcohol in the presence of a catalyst such as an organic acid, for example an aromatic acid, an inorganic acid such as sulfuric acid, hydrochloric acid and the like, a Lewis acid such as boron fluoride etherate, a cation exchange resin, reacting with an O-alkylating agent such as diazomethane, reacting with a dialkyl sulfate or with an alkyl halide. This procedure is per se well known in the art and one skilled in the art would be fully capable of conducting such a procedure being fully aware of the time, temperature and solvents to be selected. For example, when compounds of the formula (I) have a carboxylic acid methyl ester or a carboxylic acid benzyl ester at Y, the compound is obtained by treating the corresponding carboxylic acid with methyl alcohol or benzyl alcohol, respectively, in the presence of a suitable catalyst such as a mineral acid, for example sulfuric acid, hydrochloric acid and the like, an organic acid such as an aromatic sulfonic acid, a Lewis acid such as boron fluoride etherate or a cation exchanger resin. The reaction temperature will generally be in the range of from about room temperature to about 100° C. The reaction time will generally be within the range of fifty minutes to fifty hours. The reaction time and its dependency upon the reactants used would be well appreciated by one skilled in the art.

After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein Y is a carboxylic acid amide are produced from a compound of the formula (I) wherein Y is a carboxylic acid ester by per se known techniques wherein the carboxylic acid ester moiety is converted to a carboxylic acid amide, for example, a compound of the formula (I) wherein Y is a carboxylic acid ester is treated with concentrated ammonia water or with liquid ammonia to produce a compound of the formula (I) in which Y is a carboxylic acid amide. The reaction may be accelerated by the addition of a catalyst such as ammonium chloride, sodium methoxide, sodium amide or butyl lithium. The reaction temperature will generally be from about −70° C. to room temperature. The reaction time will generally be within the range of fifty minutes to fifty hours. The reaction time and its dependency upon the reactants used would be well appreciated by one skilled in the art.

After the reaction is complete; the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) wherein Y is CH$_2$OH are produced by treating a compound of the formula (I) in which Y is a carboxylic acid ester with a reducing agent which does not affect any of the other groups. Suitable reducing agents are alkoxy lithium aluminum hydride, sodium brohydride, sodium borohydride-aluminum chloride, lithium bromide to diborane, preferably lithium borohydride. The reduction procedure is per se well known in the art and one skilled in the art would be fully capable of conducting such a reduction procedure being fully aware of the time, temperature and solvents to be selected. Examples of solvents are ethyl ether, tetrahydrofuran and dioxane. The reaction temperature will generally be in the range of from about 0° C. to the boiling point of the solvent. The reaction time will generally be within the range of fifty minutes to fifty hours. The reaction time and its dependency upon the reactants used would be well appreciated by one skilled in the art.

After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

Compounds of the formula (I) may also be produced by utilizing two or more of the above described methods in combination. One or more of the substituents in the initially produced product is removed by one of the procedures known in the art and described generally above and then subsequent conversion to the final product is achieved by utilizing a further procedure described above. In the methods described hereinabove, functional group(s) in the compound (I) may be protected before the reaction with a general protective group and then said protective group is removed therefrom.

For example, a compound of the formula (I) in which both R$^3$ and R$^4$ are hydrogen and R$^7$ is hydrogen or lower alkyl may be treated to introduce a protective group onto the amino group using known protecting procedures to produce a compound of the formula (V) as hereinbefore defined in which P is a protective group for the amino group. That compound is then alkylated according to the procedure described above whereby the phenolic hydroxyl group is alkylated and, if necessary, deprotection of the amino group and/or hydrolysis of the ester may be conducted to produce a compound of the formula (IV) in which R$^{111}$ is lower alkyl, R$^{31}$ is hydrogen or a protective group and R$^{71}$ is hydrogen or lower alkyl:

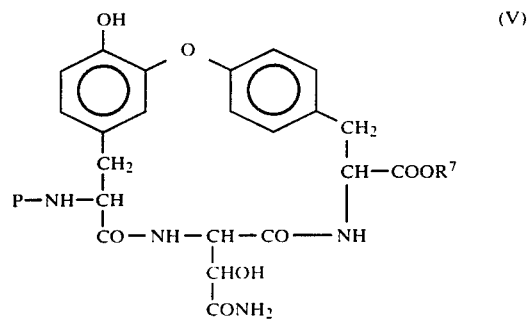

(V)

wherein P is hydrogen or a protective group for the amino group and R$^7$ is hydrogen or alkyl of 1 to 10 carbon atoms;

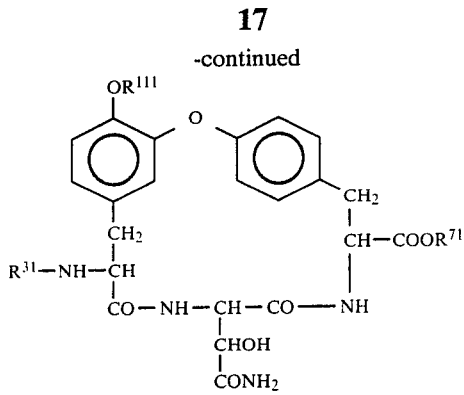

$$\text{(VI)}$$

wherein $R^{111}$ is alkyl of 1 to 10 carbon atoms; $R^{31}$ is hydrogen or a protective group for the amino moiety; and $R^{71}$ is hydrogen or alkyl of 1 to 10 carbon atoms.

Examples of suitable protective groups for the amino moiety are urethane type protective groups such as benzyloxycarbonyl, acyl type protective groups such as formyl, as well as other protective groups known per se in the art.

Methods for removal of the protective group will vary depending upon the particular protective group utilized and those skilled in the art would be familiar with suitable procedures for removal of the protective group on the amino moiety. For example, a benzyloxycarbonyl protective group can be removed by catalytic reduction and the formyl group can be removed by treatment with an acid or an alkali. Hydrolysis of an ester may be used using a suitable solvent such as water or a water-soluble organic solvent such as ethyl alcohol, methyl alcohol, N,N-dimethylformamide and the like in the presence of a basic catalyst such as sodium hydroxide, potassium carbonate and the like.

For example, OF4949-II is N-formylated with a mixture of formic acid and acetic anhydride and then reacted with an alkyl halide in the presence of a solvent such as N,N-dimethylformamide and a base such as potassium carbonate, the resulting intermediate is then treated with 4N sodium hydroxide solution so that both the N-formyl group and the alkyl ester are simultaneously hydrolyzed whereupon a compound of the formula (VI) wherein $R^{111}$ is lower alkyl and both $R^{31}$ and $R^{71}$ are hydrogen is obtained.

When methyl iodide is used as the alkyl halide, OF4949-I (compound 13) is obtained starting from OF4949-II.

After the reaction is complete, the desired product can be isolated and purified by procedures per se known in the art such as concentration, extraction with a suitable solvent, transfer to another solvent, crystallization, ion exchange chromatography, adsorption chromatography and partition chromatography.

The compounds of the present invention exhibit immunomodulating action against living organisms and anti-inflammatory action inhibiting the bradykinin formation.

The inhibition of aminopeptidase B activity can be measured by the method of V. K. Hops et al (V. K. Hops, K. K. Makinen, G. G. Glenner: Archives of Biochemistry and Biophysics, 144, 557, 1966) with the following modifications:

0.1 ml of Hanks solution (manufacture of Nissui Pharmaceutical Co., Ltd.) in which 3 mM arginine-beta-naphthylamide is dissolved is added 0.7 ml of Hanks solution containing the sample to be measured, the mixture is heated at 37° C. for three minutes, 0.2 ml of Ehrlich carcinoma cells suspension is added thereto to make the cell concentration $2.5 \times 10^7$/ml, then the mixture is kept at 37° C. for thirty minutes, 1.0M acetic acid buffer (pH 4.2) containing 0.3 mg/cc of garnet GBC (diazonium salt of o-aminotoluene) (manufacture of Sigma Co.) and 3% of Tween 20 (Wako Pure Drugs Co.) is then added, the mixture is allowed to stand at room temperature for fifteen minutes, and the extinction (a) at 525 nm of the supernatant liquid is measured.

At the same time, the extinction (b) of the control solution which is only Hanks solution without the sample to be tested is measured and the inhibitory ratio of aminopeptidase B is calculated from the following expression:

$$(b-a)/b \times 100$$

The Ehrlich carcinoma cells used hereinabove are those maintained by subculture in peritoneal cavity of ddY strain mice of 4 to 6 weeks age and are suspended by transferring $2 \times 10^6$ cells into the peritoneal cavity of mice followed by isolating from the ascites after 7 to 10 days. The cells suspension is prepared by treating the ascites containing the Ehrlich carcinoma cells with Tris-ammonium chloride solution (pH 7.2), removing erythrocytes therefrom, washing with Hanks solution for three times, and diluting with the Hanks solution to certain cell concentration. This is a uniform cell group containing not less than 96% living cells of Ehrlich carcinoma.

By way of the test method as given above, inhibitory ratio of OF4949 and derivatives thereof at various concentrations are calculated and the 50% inhibitory concentration for each is measured. Results of the test with representative compounds of the present invention are given in Table 7.

TABLE 7

| Compounds | 50% Inhibitory Concn ($\mu$g/ml) |
| --- | --- |
| OF4949-I | 0.0054 |
| OF4949-II | 0.0048 |
| No. 1 | 0.0056 |
| 2 | 1.35 |
| 3 | 0.095 |
| 4 | 0.025 |
| 5 | 0.54 |
| 6 | 3.6 |
| 11 | 12.5 |
| 14 | 0.0052 |
| 15 | 0.0117 |
| 16 | 0.0155 |
| 17 | 0.016 |
| 18 | 0.25 |
| 19 | 0.040 |
| 21 | 0.30 |
| 22 | 2.2 |
| 28 | 10.6 |
| 29 | 0.86 |
| 30 | 14.0 |
| 31 | 0.025 |
| 32 | 0.156 |

The compounds of the present invention also exhibit potentiating action on cellular immunity measured with a delayed type hypersensitivity, hereinafter referred to as DTH, by innoculation of sheep erythrocyte to hind paws of mice. Thus, sheep erythrocytes are used as antigen and $1 \times 10^5$ of them are subjected to intravenous injection to $CDF_1$ strain female mice of 10 weeks of age (8 mice per group) and, immediately after the sensitization, a solution of OF4949 or derivatives thereof in a sterilized water is injected intraperitoneally with dosages of 5, 50 or 500 μg/kg and, after four days, $10^8$ sheep erythrocytes are injected subcutaneously into left hind paws of the mice. After 24 hours, the degree of edema, i.e. thickness of the paws at that time, observed at the hind paws is measured using a slide calipers. Results of the test with the representative compounds of the present invention are given in Table 8 below.

TABLE 8

| Compounds | Doses (μg/kg) | Thickness of Edema (× 0.1 mm) (Mean Value ± Standard Error) | Potentiating Ratio to Control (%) |
|---|---|---|---|
| (Test 1) | control | 7.2 ± 0.3 | 100 |
| OF4949-I | 5 | 9.5 ± 0.6 | 132 |
|  | 50 | 11.7 ± 1.5 | 163 |
|  | 500 | 9.1 ± 0.5 | 126 |
| (Test 2) | control | 9.2 ± 1.0 | 100 |
| OF4949-II | 5 | 11.7 ± 1.9 | 127 |
|  | 50 | 13.5 ± 1.2 | 147 |
|  | 500 | 11.4 ± 2.6 | 124 |
| (Test 3) | control | 8.0 ± 0.5 | 100 |
| Compd. 2 | 5 | 9.3 ± 1.2 | 116 |
|  | 50 | 9.1 ± 1.1 | 114 |
|  | 500 | 10.2 ± 0.9 | 128 |
| (Test 4) | control | 7.0 ± 0.3 | 100 |
| Compd. 17 | 5 | 8.8 ± 0.7 | 126 |
|  | 50 | 8.4 ± 0.7 | 120 |
|  | 500 | 8.5 ± 0.7 | 121 |
| Compd. 18 | 5 | 8.2 ± 0.7 | 117 |
|  | 50 | 8.5 ± 0.7 | 121 |
|  | 500 | 7.5 ± 0.6 | 107 |
| Compd. 21 | 5 | 7.8 ± 0.8 | 111 |
|  | 50 | 7.8 ± 0.7 | 111 |
|  | 500 | 8.7 ± 0.8 | 124 |

The compounds of the present invention are also characterized by a very low toxicity, making their administration to humans and animals facile. Acute toxicity tests injecting 300 mg/kg intraperitoneally of representative compounds of the present invention to ICR strains of mice produced the toxicity results set forth in Table 9 below:

TABLE 9

| Compounds | Test Results |
|---|---|
| OF4949-I | No toxicity is observed |
| OF4949-II | " |
| Compd. 17 | " |
| 21 | " |
| 22 | " |
| 28 | " |
| 29 | " |

Suitable pharmaceutical compositions according to the present invention may contain from 0.01% to 99.5% of a compound of the formula (I) or a pharmaceutically acceptable salt thereof or more preferably from about 5% to about 95%. Such pharmaceutical compositions are preferably in dosage unit form; i.e., physically discrete units containing a predetermined amount of the compound of the formula (I) or a pharmaceutically acceptable salt thereof corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day.

Although the dosage and dosage regimen must in each case be carefully adjusted, utilizing sound professional judgment and considering the age, weight and condition of the recipient, the route of administration and the nature and gravity of the illness, generally the dosage for an average human will be as follows: for oral administration from about 10 to about 1000 mg 1 to 4 times per day of said compound or salt thereof for an average adult. For parenteral administration, from about 0.1 to about 300 mg one to four times per day. For rectal administration, from about 0.1 to about 300 mg one to four times per day. For inhalation and nasal administration, from about 0.1 to about 200 mg one to three times per day. For topical application such as ointment, from about 1 to about 1000 mg one to three times per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acceptable salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

The compounds of the present invention may also be administered rectally by formulating a composition according to the present invention using procedures per se known into a suppository, for example by mixing a compound of the present invention with a low melting and water-soluble or insoluble solid such as, for example, polyethylene glycol, cocoa butter, higher esters such as myristyl palmitate or mixtures thereof.

The pharmaceutical compositions according to the present invention may contain compounds of the present invention as the sole therapeutic agent or the compounds of the present invention may be present as part of a combination with such other pharmaceuticals as, for example, cytosine arabinoside, adriamycin or mitomycin.

Alternatively, compositions may be formulated containing the compound of the present invention as the sole active agent and such compositions may be administered simultaneously or sequentially with compositions containing other therapeutics such as those above noted for combination thereby.

Figure 1:
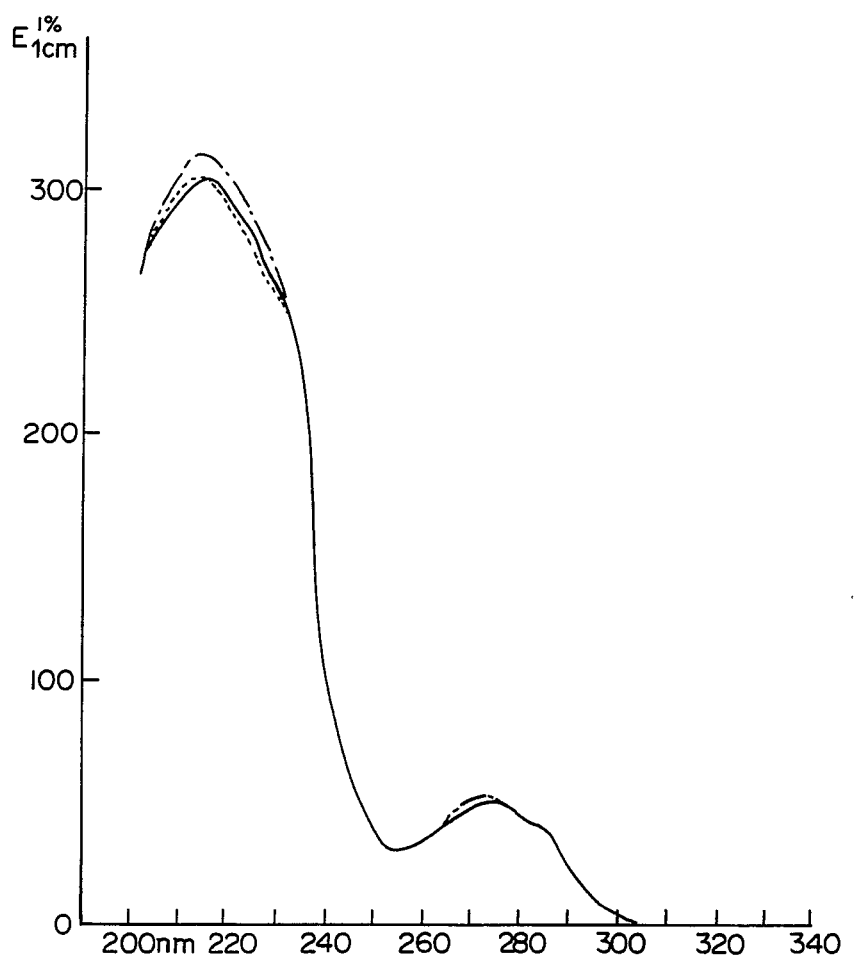
FIG. 1 is an ultraviolet absorption spectra chart of the substance OF4949-I. In the figure, — is an absorption when the solvent is water, - - - - is an absorption when the solvent is 0.05N hydrochloric acid, and —·— is an absorption when the solvent is 0.05N sodium hydroxide.
Figure 2:
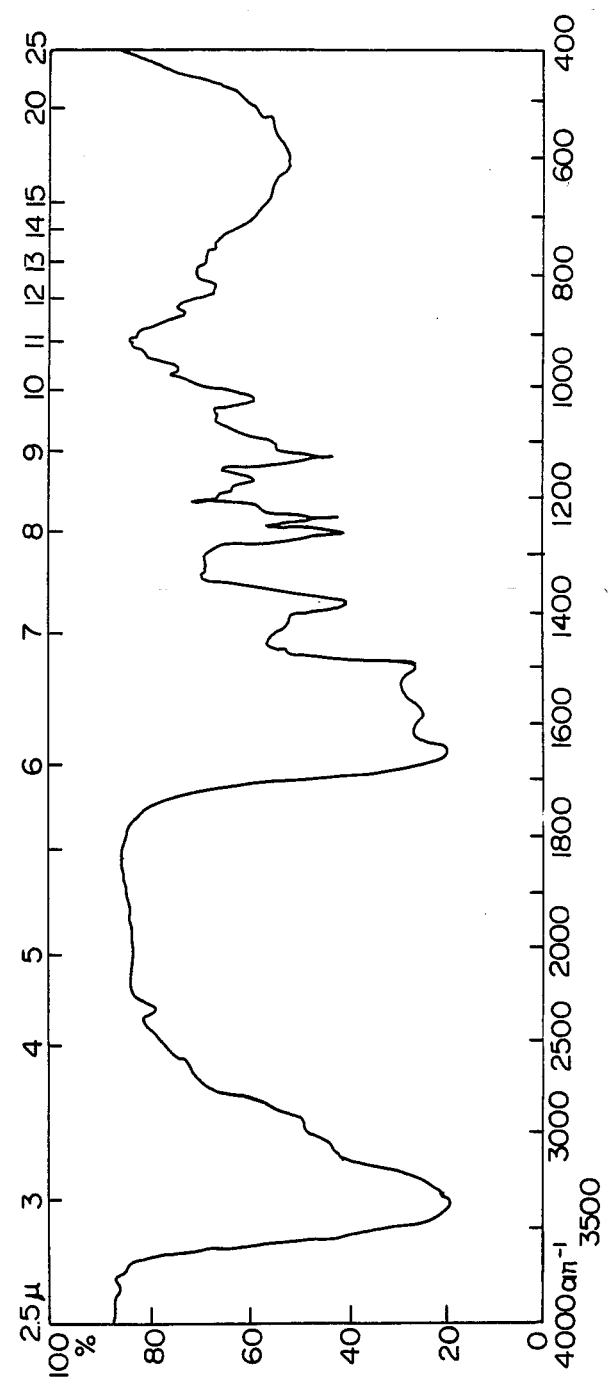
FIG. 2 is an infrared absorption spectra chart of the substance OF4949-I measured in potassium bromide.
Figure 3:
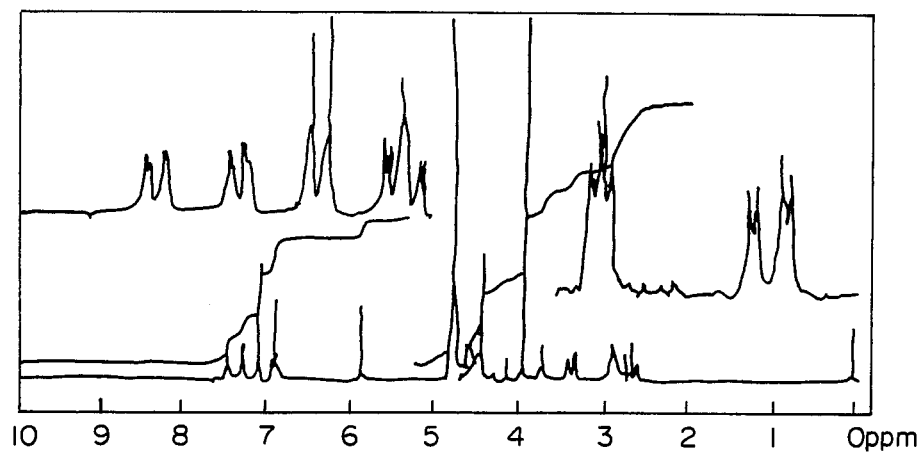
FIG. 3 is a proton nuclear magnetic resonance spectra chart of the substance OF4949-I measured in 0.06N heavy ammonia water (internal standard: DSS).
Figure 4:
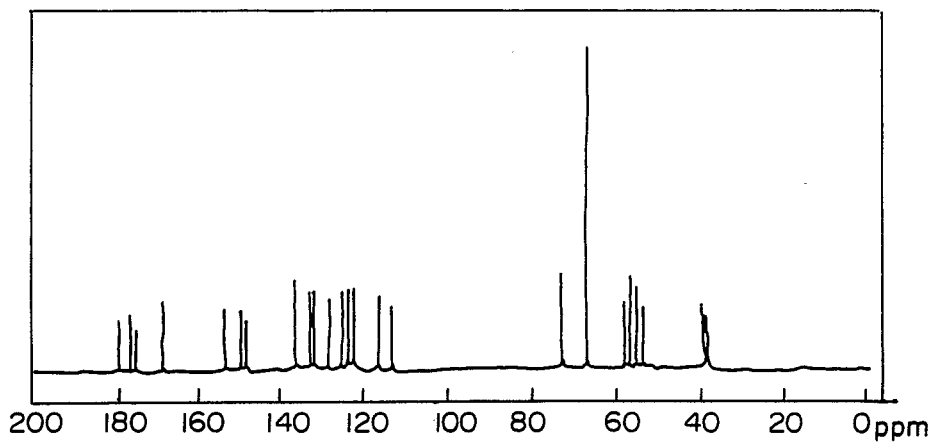
FIG. 4 is a $^{13}C$ nuclear magnetic resonance spectra of the substance OF4949-I measured in 0.06N heavy ammonia water. (internal standard: p-dioxane 67.4 ppm).
Figure 5:
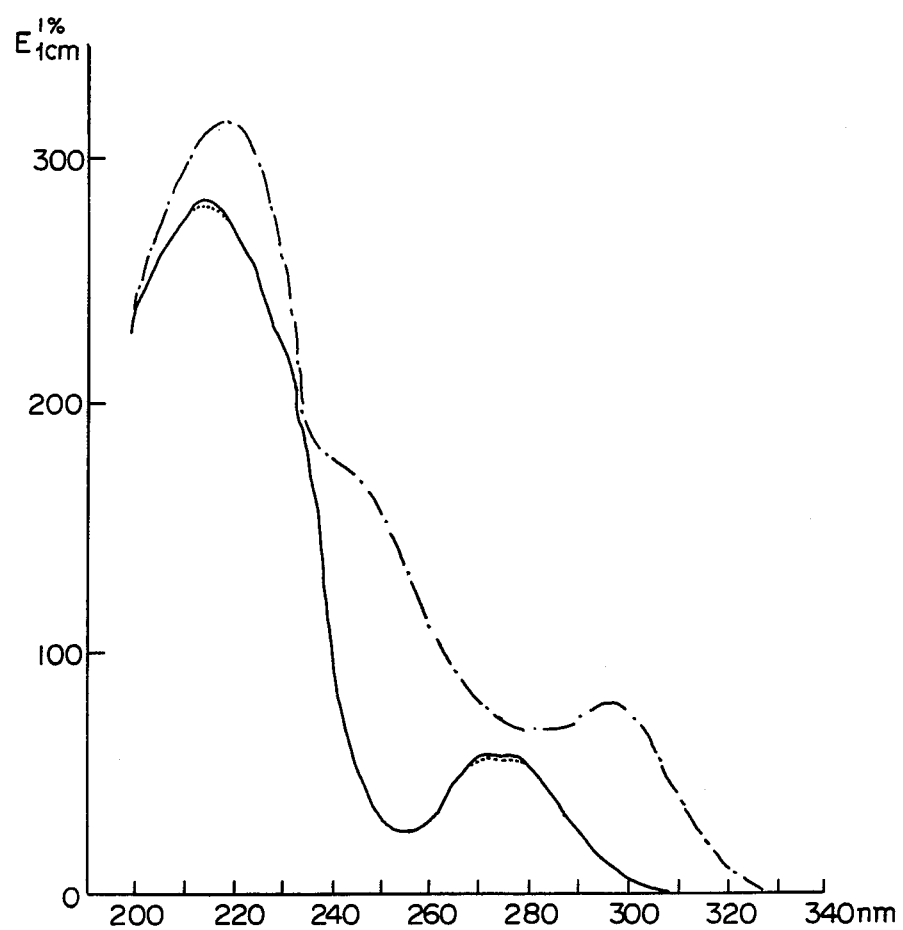
FIG. 5 is an ultraviolet absorption spectra chart of the substance OF4949-II. In the figure, — is an absorption when the solvent is water, - - - - is an absorption when the solvent is 0.05N hydrochloric acid, and —·— is an absorption when the solvent is 0.05N sodium hydroxide.
Figure 6:
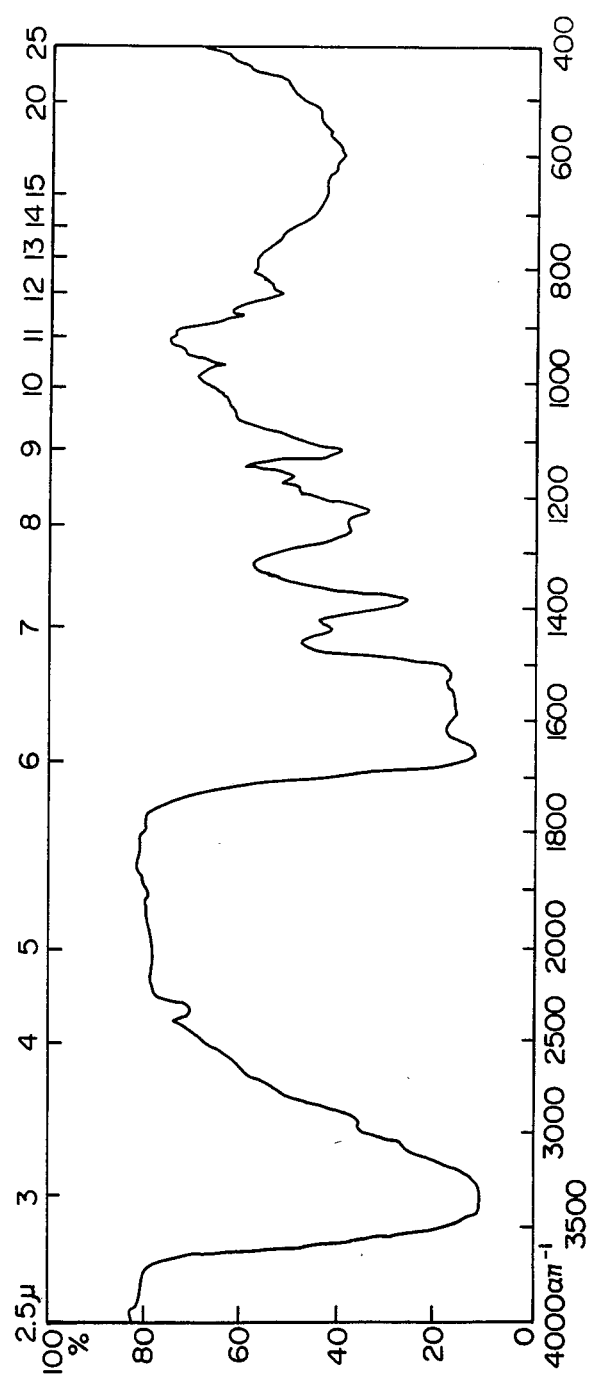
FIG. 6 is an infrared absorption spectra chart of the substance OF4949-II measured in potassium bromide.
Figure 7:
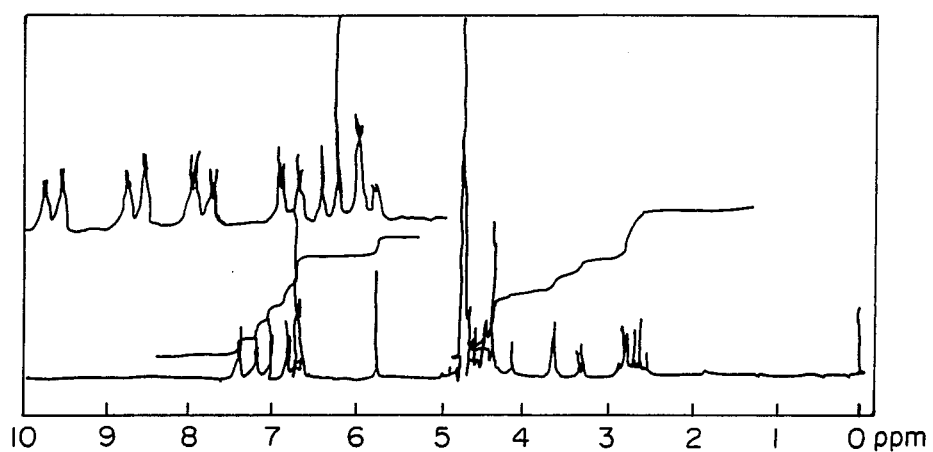
FIG. 7 is a proton nuclear magnetic resonance spectra chart of the substance OF4949-II measured in 0.06N heavy ammonia water (internal standard: DSS).
Figure 8:
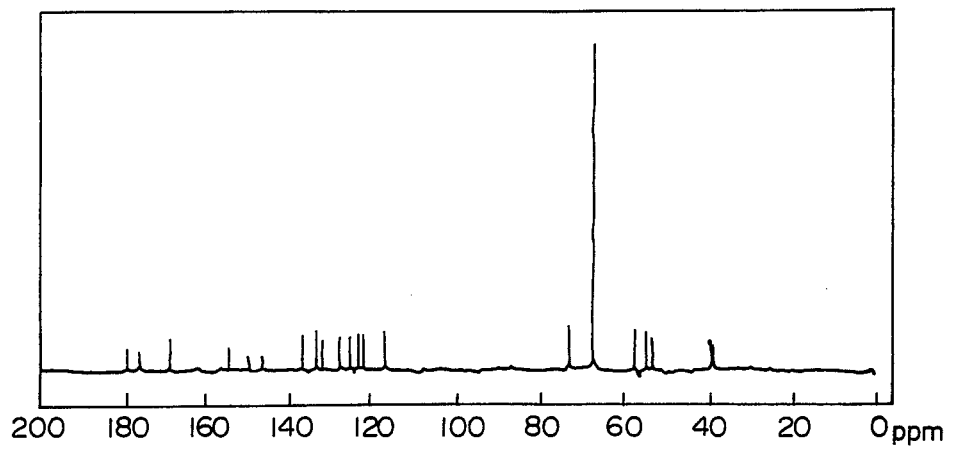
FIG. 8 is a $^{13}C$ nuclear magnetic resonance spectra of the substance OF4949-II measured in 0.06N heavy ammonia water (internal standard: p-dioxane 67.4 ppm).

The following non-limitative examples more particularly illustrate the present invention:

EXAMPLE 1. PREPARATION OF OF4949 (STEP 1)

*Penicillium rugulosum* OF4949 (FERM BP-203) is cultured for seven days on malt extract-agar slant. One loopfl spore therefrom is inoculated on 500 ml medium containing 2% of glucose, 0.5% of polypeptone, 0.1% of yeast extract, 0.05% of potassium dihydrogenphosphate and 0.05% of magnesium sulfate which is previously placed in 2 liter flask and sterilized at 120° C. for 20 minutes. This is cultured for six days at 27° C. with shaking at 190 rotations per minutes. The resulting culture is inoculated at the rate of 1 liter per tank to 15 stainless steel fermentation tanks (30 liters volume) containing sterilized 20 liters of medium containing 2% of gluocse, 0.5% of polypeptone, 0.1% of yeast extract, 0.05% of potassium dihydrogenphosphate and 0.05% of magnesium sulfate. The incubation is conducted at 27° C. with 20 liter per minute of aeration and 300 rotations per minute of rotation and, if necessary, antifoaming agent is added thereto during the incubation. The incubation is conducted for four days, the culture is then taken out, mycelia are filtered to separate culture filtrate therefrom, and 6.5 liters (compressed volume) of mycelia and 300 liters of culture filtrate are obtained.

EXAMPLE 2. PREPARATION OF OF4949 (STEP 2)

Mycelia obtained in Example 1 are extracted thrice with 24 liters of 50% acetone-water and the combined extract (72 liters) is concentrated to 30 liters in vacuo to remove acetone. The concentrate (30 liters) and 300 liters of culture filtrate obtained in Example 1 are adsorbed in a column of activated charcoal, the column is well washed with 80 liters of water, and eluted with 150 liters of hydrochloric acid solution (pH 2) containing 50% acetone. The fraction (80 liters) showing aminopeptidase inhibiting activity is concentrated to 30 liters in vacuo to remove acetone, the concentrate (30 liters) is passed through a column (1.2 liters) of strongly basic anion exchange resin Dowex 1×2 (Cl⁻ form) and the column is eluted with water. The eluate (80 liters) is adjusted to pH 3, adsorbed in a column (2.0 liters) of strongly acidic cation exchange resin Dowex 50W (H⁺ form), the column is washed with 10 liters of water, and eluted with 100 liters of 1.0N ammonia water. The active fraction (60 liters) is neutralized with 2N hydrochloric acid and adsorbed with 2 liters of non-ionic adsorption resin Diaion HP-20. The resin is washed with 20 liters of water and eluted with 20 liters of 50% methanol-water. The resulting active fraction is concentrated in vacuo to afford 28.8 grams of crude substance.

EXAMPLE 3. PREPARATION OF OF4949 (STEP 3)

Crystalline cellulose (Avicel) (30 grams) is sprinkled over 28.8 grams of crude substance obtained in Example 2, the mixture is well dried in vacuo, and filled in the upper part of 1 liter column of Avicel. This is developed with 12 liters of developer (1N ammonia water and n-butyl alcohol in 15:85 ratio) to afford an active fraction mainly composed of OF4949-I and then another active fraction mainly composed of OF4949-II. Each active fraction is neutralized with 1N hydrochloric acid, concentrated in vacuo, then dissolved in water once again, and adsorbed with 500 ml of Diaion HP-20. The resin is washed with water, eluted with 2 liters of 50% methanol-water, and the resulting active fraction is concentrated in vacuo to afford each 3.1 grams of OF4949-I crude powder and 4.1 grams of OF4949-II crude powder.

EXAMPLE 4. PREPARATION OF OF4949 (STEP 4)

Crude power (3.1 grams) of OF4949-I obtained in Example 3 is dissolved in 15 ml of water and the solution is subjected to a reverse phase partition chromatography using high-performance liquid chromatography (System 500, Waters Co) exclusively for large amount under the condition of applying a developer of 0.1M citric acid buffer and acetonitrile (90:10 ratio) and a column of a cartrige column ($C_{18}$, Waters Co.) to assay the aminopeptidase B inhibitory activity. The active fraction is adsorbed with 200 ml of Diaion HP-20, the resin is washed with water, and eluted with 1 liter of 50% methanol-water. The active fractions are collected, concentrated in vacuo, and lyophilized to afford 455 mg of OF4949-I.

Another crude powder (4.1 grams of OF4949-II) obtained in Example 3 is similarly subjected to a $C_{18}$ reverse phase partition chromatography using a developer of 0.1M citric acid buffer and acetonitrile (95:5 ratio) followed by a column chromatography with Diaion HP-20 to afford 671 mg of OF4949-II.

EXAMPLE 5. MANUFACTURE OF COMPOUND 2

OF4949-II (223.7 mg) is dissolved in 10 ml of 1N hydrochloric acid, the solution is placed in a sealed tube, and heated at 100° C. for seven hours. The reaction mixture is evaporated to dryness, the residue is dissolved in 10 ml of water, and developed with a high-performance liquid chromatography using nucleosil 30 $C_{18}$ (2.0×25.0 cm) as a column and a mixture of 0.1M citric acid buffer and acetonitrile as a developer to afford a fraction containing the compound 2.

Said fraction is then adsorbed with 250 ml of strongly acidic cation exchange resin Dowex 50W (H+ form), the column is washed with water, and eluted with 1N ammonia water. The eluate containing the compound 2 is concentrated in vacuo, the residue is dissolved in 5 ml of water, adsorbed with a column (2.0×25.0 cm) of Nucleosil 30 $C_{18}$, and eluted with water. The resulting eluate containing the compound 2 is concentrated and dried to give 78.8 mg of colorless powder of the compound 2.

EXAMPLE 6. MANUFACTURE OF COMPOUND 10

OF4949-II (50 mg) is dissolved in 5 ml of 0.1M phosphate buffer (pH 7.0), 100 μl of formaline is added thereto, the mixture is stirred for ten minutes at room temperature, and stirred another one hour at room temperature with 30 mg of sodium cyanoborohydride. The reaction mixture is developed with a high-performance liquid chromatography using 2.0×25.0 cm column of Nucleosil 30 $C_{18}$ and a mixture of 0.1M citric acid buffer (pH 5.7) and acetonitrile as a developer to afford a fraction containing the compound 10. Said fraction is concentrated, the concentrate is adsorbed with 20 ml of Diaion HP-20, the resin is washed with water, eluted with 50% methanol-water, and the eluate is concentrated to dryness to afford 24.6 mg of colourless powder of the compound 10.

EXAMPLE 7. MANUFACTURE OF THE COMPOUND 12

OF4949-II (60 mg) is dissolved in 5 ml of 0.1M phosphate buffer (pH 7.0) and the solution is stirred for ten minutes at room temperature with 50 μl of acetaldehyde. Then 30 mg of sodium cyanoborohydride is added thereto and the mixture is stirred at room temperature for another one hour. The reaction solution is developed with a high-performance liquid chromatography using 2.0×25.0 cm column of Nucleosil 30 $C_{18}$ and a mixture of 0.1M citric acid buffer (pH 5.7) and acetonitrile as a developer to afford a fraction containing the compound 12.

Said fraction is concentrated, the concentrate is adsorbed with 20 ml of Diaion HP-20, the resin is washed with water, then eluted with 50% methanol-water, and the eluate is concentrated to dryness to afford 31.4 mg of colourless powder of the compound 12.

EXAMPLE 8. MANUFACTURE OF THE COMPOUNDS 7, 23 AND 13

To 267 mg of the compound 6 are added 20 ml of N,N-dimethylformamide, 200 mg of potassium carbonate and 200 μl of methyl iodide and the mixture is stirred at room temperature for 24 hours. The reaction solution is neutralized and developed with a high-performance liquid chromatography using 2.0×25.0 cm column of Nucleosil 30 $C_{18}$ and a mixture of 0.1M citric acid buffer (pH 5.7) and acetonitrile as a developer to afford two fractions containing the compound 7 and the compound 23, respectively.

Each fraction is concentrated, the concentrate is adsorbed with 20 ml of Amberlite XAD-2 (Organo), the resin is washed with water, eluted with methyl alcohol, the eluate is concentrated to dryness, and 52.3 mg of colourless powder of the compound 7 and 137.2 mg of colourless powder of the compound 23, each, are obtained.

To 42.2 mg of the powder of the compound 23 is added 20 ml of 4N sodium hydroxide solution, the mixture is stirred at room temperature for thirty minutes, neutralized with 2N hydrochloric acid, adsorbed with 20 ml of Diaion HP-20, the resin is washed with water, eluted with 50% methanol-water, and the eluate is concentrated to dryness to afford 39.0 mg of colourless powder of the compound 13 which is identical with OF4949-I.

EXAMPLE 9. MANUFACTURE OF THE COMPOUNDS 14, 1, 3 and 19

To 67.8 mg of OF4949-I is added 10 ml of 0.2N hydrochloric acid in methyl alcohol, the mixture is stirred overnight at room temperature, and concentrated to dryness. The residue is dissolved in 10 ml of water and the solution is developed with a high-performance liquid chromatography using 2.0×25.0 cm column of Nucleosil 30 $C_{18}$ and a mixture of 0.1M citric acid buffer and acetonitrile as a developer to afford a fraction containing the compound 14.

Said fraction is concentrated, the concentrate is adsorbed with 20 ml of Amberlite XAD-2, the resin is washed with water, then eluted with 50% methanol-water, and the eluate is concentrated to dryness to afford 30.6 mg of colourless powder of the compound 14.

Similarly are prepared 74.3 mg of the compound 1, 55.5 mg of the compound 3 and 22.3 mg of the compound 19 from 91 mg of OF4949-II, 90.4 mg of the compound 2, and 33.8 mg of the compound 18, respectively.

Alternatively, 11 mg of OF4949-I is suspended in 10 ml equivolume mixture of methyl alcohol and ether, diazomethane is passed into the suspension and, when the crystals therein are dissolved, the mixture is concentrated to dryness. The resulting residue is dissolved in 0.5 ml of water and the solution is purified with a high-performance liquid chromatography and Amberlite XAD-2 the same as above to afford 3.6 mg of colourless powder of the compound 14. Similarly is prepared 1.9 mg of the compound 19 from 10.5 mg of the compound 18.

EXAMPLE 10. MANUFACTURE OF THE COMPOUND 15

To 200 mg of OF4949-II are added 10 ml of N,N-dimethylformamide and 10 ml of 2N hydrochloric acid in butyl alcohol and the mixture is stirred overnight at room temperature. The reaction solution is dissolved in 200 ml of water, the solution is adsorbed with 20 ml of Amberlite XAD-2, the resin is washed with water, and eluted with 50% methanol-water. The fraction containing the compound 15 is concentrated to dryness to afford 72.9 mg of the colourless powder of the compound 15.

EXAMPLE 11. MANUFACTURE OF THE COMPOUND 16

To 200 mg of OF4949-I is added 10 ml of 2N hydrochloric acid in benzyl alcohol and the mixture is stirred overnight at room temperature. To the reaction solution is added 50 ml of 1:1 mixture of hexane and chloroform and the resulting precipitate is collected by filtration and dried to give 196.2 mg of the mass. This is dissolved in 1 ml of dimethyl sulfoxide and the solution is developed with a high-performance liquid chromatography using a 2.0×25.0 cm column of Nucleosil 30 $C_{18}$ and a mixture of acetonitrile and 0.1M citric acid buffer as a developer to afford a fraction containing the compound 16.

Said fraction is concentrated, the concentrate is adsorbed with 20 ml of Amberlite XAD-2, the resin is washed with water, then eluted with methyl alcohol, and the eluate is concentrated to dryness to give 19.1 mg of colourless powder of the compound 16.

Alternatively, 200 mg of OF4949-I is mixed with 10 ml of benzyl alcohol, 20 ml of benzene and 100 mg of p-toluenesulfonic acid and the mixture is heated to reflux for four hours. To the reaction solution is added 100 ml of a mixture of ether and hexane (1:1), the resulting precipitate is collected by filtration, and dried to afford 343.7 mg of the mass. Said mass is dissolved in 2 ml of dimethyl sulfoxide and the solution is developed with a high-performance liquid chromatography with a column of 2.0×25.0 cm Nucleosil 30 $C_{18}$ and a mixture of acetonitrile and 0.1M citric acid buffer as a developer to afford a fraction containing the compound 16.

Said fraction is concentrated, the concentrate is adsorbed with 20 ml of Amberlite XAD-2, the resin is washed with water, then eluted with methyl alcohol, and the eluate is concentrated to dryness to afford 83.8 mg of colourless powder of the compound 16.

EXAMPLE 12. MANUFACTURE OF THE COMPOUND 17

To 102 mg of the compound 14 is added 5 ml of concentrated ammonia water and the mixture is stirred for overnight at room temperature. The reaction solution is neutralized with 6N hydrochloric acid and developed with a high-performance liquid chromatography using a 2.0×25.0 cm column of Nucleosil 30 $C_{18}$ and a mixture of 0.1M citric acid buffer and acetonitrile as a developer to afford a fraction containing the compound 17.

Said fraction is concentrated, the concentrate is adsorbed with 20 ml of Diaion HP-20, the resin is washed with water, then eluted with 50% methanol-water, and the eluate is concentrated to dryness to afford 48.3 mg of colourless powder of the compound 17.

Similarly is prepared 30.8 mg of the compound 17 from the compound 19 (59.6 mg).

EXAMPLE 13. MANUFACTURE OF THE COMPOUND 18

OF4949-I (1.0 gram) is dissolved in 20 ml of 1N hydrochloric acid and heated in a sealed tube at 100° C. for seven hours. The reaction solution is concentrated to dryness, the residue is dissolved in 10 ml of water, and the solution is developed by a high-performance liquid chromatography using a column of PrepPAK-500/$C_{18}$ (Waters) and a mixture of 0.1M citric acid buffer and acetonitrile as a developer to afford a fraction containing the compound 18.

Said fraction is concentrated, the concentrate is adjusted to pH 3 with 6N hydrochloric acid, adsorbed with Diaion HP-20 (70 ml), the resin is washed with water, then eluted with 50% methanol-water, and the eluate is concentrated. The resulting crystals are obtained by filtration to give 345.4 mg of colourless column of the compound 18. It shows no clear melting point until 300° C. Elementary analysis calculated for $C_{23}H_{25}N_3O_9 \cdot 2H_2O$: C 52.77, H 5.58, N, 8.03; Found: C 53.01, H 5.83, N 8.09.

EXAMPLE 14. MANUFACTURE OF THE COMPOUND 20

To 59.6 mg of the compound 19 is added 3 ml of concentrated ammonia water and the mixture is stirred at room temperature overnight. The reaction solution is diluted with 3 ml of water and developed with a high-performance liquid chromatography using a column (2.0×25.0 cm) of Nucleosil 30 $C_{18}$ and a mixture of 0.1M citric acid buffer and acetonitrile as a developer to afford a fraction containing the compound 20.

Said fraction is concentrated, the concentrate is adsorbed with 20 ml of Diaion HP-20, the resin is washed with water, and eluted with 50% methanol-water. The eluate is concentrated to dryness to afford 9.2 mg of colourless powder of the compound 20.

EXAMPLE 15. MANUFACTURE OF THE COMPOUNDS 21, 4 AND 5

To 462.2 mg of the compound 19 is added 40 ml of tetrahydrofuran and the mixture is heated to reflux with 500 mg of lithium borohydride for six hours. To the reaction solution is added 2N hydrochloric acid in methyl alcohol so that an excess of lithium borohydride is comsumed. Then the mixture is concentrated to dryness, the residue is dissolved in 10 ml of water, and the solution is developed by a high-performance liquid chromatography using a column (2.0×25.0 cm) of Nucleosil 30 $C_{18}$ and a mixture of 0.1M citric acid buffer and acetonitrile as a developer to afford a fraction containing the compound 21. Said fraction is concentrated, the concentrate is adsorbed with 20 ml of Diaion HP-20, the resin is washed with water, eluted with 50% methanol-water, and the eluate is concentrated to dryness to afford 233.6 mg of colourless powder of the compound 21. Similarly prepared are 6.1 mg of the compound 4 and 12.0 mg of the compound 5 from 37 mg of the compound 1 and 40 mg of the compound 3, respectively.

EXAMPLE 16 MANUFACTURE OF THE COMPOUNDS 22 AND 6

To 100 mg of OF4949-I is added 5 ml of 98% formic acid and, with ice cooling and stirring, 5 ml of acetic anhydride is dropped thereinto. Then the mixture is stirred for 30 minutes with ice-cooling and allowed to stand at room temperature for one hour. To the resulting reaction solution is added 10 ml of water, the mixture is stirred for ten minutes and concentrated. The concentrate is developed by a high-performance liquid chromatography with a 2.0×25.0 cm column of Nucleosil 30 $C_{18}$ and a mixture of 0.1M citric acid buffer and acetonitrile as a developer to afford a fraction containing the compound 22.

Said fraction is concentrated, the concentrate is adsorbed with 20 ml of Diaion HP-20, the resin is washed with water, and eluted with 50% methanol-water. The resulting eluate containing the compound 22 is concentrated and filtered to afford 42.2 mg of colourless microneedles of the compound 22. It shows no clear melting point until 300° C. Elementary analysis calculated for $C_{24}H_{26}N_4O_9$: C 56.03, H 5.09, N 10.89 Found: C 55.87, H 5.08, N 10.94.

Similarly is prepared 24.1 mg of the compound 6 from 60 mg of OF4949-II.

EXAMPLE 17. MANUFACTURE OF THE COMPOUND 24

To 134.0 mg of the compound 22 are added 10 ml of N,N-dimethylformamide 100 mg of potassium carbonate and 200 µl of n-butyl bromide and the mixture is stirred overnight at room temperature. The reaction solution is neutralized and developed by a high-performance liquid chromatography with a 2.0×25.0 cm column of Nucleosil 30 $C_{18}$ and a mixture of 0.1M citric acid buffer and acetonitrile as a developer to afford a fraction containing the compound 24. Said fraction is concentrated, the concentrate is adsorbed with Amberlite XAD-2 (20 ml), the resin is washed with water and eluted with methyl alcohol. The eluate is concentrated to dryness to afford 59.0 mg of colourless powder of the compound 24.

EXAMPLE 18. MANUFACTURE OF THE COMPOUNDS 25 AND 8

OF4949-I (200 mg) is dissolved in 20 ml of water and. with ice cooling and stirring, 10 ml of acetic anhydride is dropped thereinto. The mixture is stirred for fifteen minutes with ice cooling and then stirred overnight at room temperature. The reaction solution is diluted with 100 ml of water, adsorbed with 20 ml of Diaion HP-20, the resin is washed with water, eluted with 50% methanol-water, the eluate containing the compound 25 is concentrated to dryness, and 156.9 mg of colourless powder of the compound 25 is obtained.

Similarly is prepared 44.9 mg of the compound 8 from 50 mg of OF4949-II.

EXAMPLE 19. MANUFACTURE OF THE COMPOUNDS 26 and 9

To 100 mg of OF4949-I are added 10 ml of methyl alcohol and 5 ml of acetic anhydride and the mixture is stirred overnight at room temperature. The reaction solution is concentrated to dryness, the residue is dissolved in 7 ml of a mixture of water and dimethyl sulfoxide, and the solution is developed by a high-performance liquid chromatography with a 2.0×25.0 cm column of Nucleosil 30 $C_{18}$ and a mixture of 0.1M citric acid buffer and acetonitrile as a developer to afford a fraction containing the compound 26. Said fraction is concentrated, the concentrate is adsorbed with 20 ml of Amberlite XAD-2, the resin is washed with water, eluted with 50% methanol-water, and the eluate is concentrated to dryness to afford 57.0 mg of colourless powder of the compound 26.

Similarly is prepared 23.3 mg of the compound 9 from 50 mg of OF4949-II.

EXAMPLE 20. MANUFACTURE OF THE COMPOUND 27

To 30.6 mg of the compound 14 are added 1 ml of pyridine and 100 µl of acetic anhydride and the mixture is stirred for four hours at room temperature. To the reaction solution is added 2 ml of water and developed by a high-performance liquid chromatography with a 2.0×25.0 cm column of Nucleosil 30 $C_{18}$ and a mixture of 0.1M citric acid buffer and acetonitrile as a developer to afford a fraction containing the compound 27. Said fraction is concentrated, the concentrate is adsorbed with 20 ml of Amberlite XAD-2, the resin is washed with water, and subjected to a gradient elution with methyl alcohol from water to afford a fraction containing the compound 27 which is further concentrated and the resulting crystals are collected by filtration to afford 12.9 mg of colourless crystals of the compound 27.

EXAMPLE 21. MANUFACTURE OF THE COMPOUNDS 28 AND 11

OF4949-I (200 mg) is dissolved in 10 ml of 0.1M phosphate buffer (pH 7.0) and the solution is stirred for ten minutes at room temperature with 40 µl of acetaldehyde. To the mixture is added 100 mg of sodium cyanoborohydride and stirred at room temperature for twenty minutes. This is concentrated to dryness, the residue is dissolved in water, and the solution is developed by a high-performance liquid chromatography with a 2.0×25.0 cm column of Nucleosil 30 $C_{18}$ and a mixture of 0.1M phosphate buffer (pH 5.7) and acetonitrile as a developer to afford a fraction containing the compound 28. Said fraction is concentrated, the concentrate is adsorbed with 20 ml of Diaion HP-20, the resin is washed with water, eluted with 50% methanol-water, and the eluate is concentrated to dryness to afford 128.9 mg of colourless powder of the compound 28.

Similarly is prepared 28.6 mg of the compound 11 from 50 mg of OF4949-II.

EXAMPLE 22. MANUFACTURE OF THE COMPOUNDS 29 AND 30

OF4949-I (200 mg) is dissolved in 20 ml of water and the solution is stirred for one hour at room temperature with 250 mg of N-bromosuccinimide. The precipitate formed in the reaction solution is dissolved by addition of a few drops of 4N ammonia water and the solution is developed by a high-performance liquid chromatography with a 2.0×25.0 cm column of Nucleosil 30 $C_{18}$ and a mixture of 0.1M citric acid buffer and acetonitrile as a developer to afford a fraction containing the compound 29.

Said fraction is concentrated, the concentrate is adsorbed in 20 ml of Amberlite XAD-2, the resin is washed with water, eluted with 50% methanol-water, the eluate containing the compound 29 is concentrated, and the crystals appeared are collected by filtration to give 75.8 mg of colourless column of the compound 29. It shows no clear melting point until 300° C. Elementary analysis calculated as $C_{23}H_{25}N_4O_8Br \cdot H_2O$: C 47.35, H 4.67, N 9.60; Found: C 46.91, H 4.93, N 9.57.

Similarly is prepared 38.6 mg of the compound 30 from 41.0 mg of the compound 18.

EXAMPLE 23. MANUFACTURE OF THE COMPOUND 31

To 278.7 mg of the compound 6 are added 20 ml of N,N-dimethylformamide, 200 mg of potassium carbonate and 500 μl of n-butyl bromide and the mixture is stirred overnight at room temperature. The reaction solution is neutralized and developed by a high-performance liquid chromatography with a 2.0×25.0 cm column of Nucleosil 30 $C_{18}$ and a mixture of 0.1M citric acid buffer and acetonitrile as a developer to give a fraction containing the n-butylated substance. Said fraction is concentrated and the resulting precipitate is collected by filtration to give 52.0 mg of powder. To 52.0 mg of the powder is added 2 ml of 4N sodium hydroxide solution, the mixtue is stirred for two hours at room temperature, neutralized, and purified by a high-performance liquid chromatography once again to afford a fraction containing the compound 31.

Said fraction is concentrated, the concentrate is adsorbed with 20 ml of Amberlite XAD-2, the resin is washed with water, and eluted with 50% methanol-water. The eluate containing the compound 31 is concentrated and the resulting crystals are collected by filtration to afford 25.5 mg of colourless microneedles of the compound 31. It shows no clear melting point until 300° C. Elementary analysis calculated as $C_{26}H_{32}N_4O_8$: C 59.08, H 6.10, N 10.60; Found: C 58.55, H 6.36, N 10.49.

EXAMPLE 24. MANUFACTURE OF THE COMPOUND 32

A mixture of 300 mg of OF4949-II and 100 mg of sodium bicarbonate is dissolved in 10 ml of water, to the solution are then added 5 ml of ether and 200 μl of carbobenzoxychloride, and the mixture is stirred at room temperature. After two hours, the mixture is adjusted to pH 3 with 2N hydrochloric acid, the resulting precipitate is collected by filtration, dried, and 365.0 mg of colourless powder is obtained.

To 365.0 mg of the powder are added 10 ml of acetic anhydride and 100 mg of sodium acetate, the mixture is stirred for three hours at room temperature, then poured over into ice water, the resulting precipitate is collected by filtration, and dried to give 383.9 mg of colourless powder.

The powder (104.2 mg) is dissolved in 10 ml of a mixture of methyl alcohol, acetic acid and water (8:2:1). To the solution is added 25 mg of 10% palladium carbon and hydrogen gas is introduced thereinto with stirring. After three hours, the reaction solution is filtered and the filtrate is concentrated to dryness. The residue is dissolved in 1 ml of methyl alcohol and the solution is developed by a high-performance liquid chromatography with a 2.0×25.0 cm column of Nucleosil 30 $C_{18}$ and a mixture of acetonitrile and 0.1M citric acid buffer to afford a fraction containing the compound 32.

Said fraction is concentrated, the concentrate is adsorbed with 20 ml of Amberlite XAD-2, the resin is washed with water, eluted with 50% methanol-water, and the eluate is concentrated to dryness to give 22 mg of colourless powder of the compound 32.

What we claim is:

1. A compound of the formula (I):

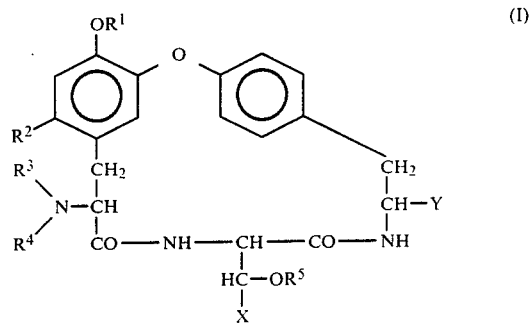

or a pharmaceutically acceptable salt thereof wherein $R^1$ is hydrogen, alkyl of 1 to 10 carbon atoms or acyl of 1 to 6 carbon atoms; $R^2$ is hydrogen or halo; $R^3$ is hydrogen, alkyl of 1 to 6 carbon atoms or acyl of 1 to 6 carbon atoms; $R^4$ is hydrogen or alkyl of 1 to 6 carbon atoms; $R^5$ is hydrogen or acyl of 1 to 6 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 10 carbon atoms or benzyl.

2. A compound according to claim 1 wherein $R^1$ is hydrogen, alkyl of 1 to 4 carbon atoms or acyl of 1 to 4 carbon atoms; $R^2$ is hydrogen, fluoro, chloro or bromo; $R^3$ is hydrogen, alkyl of 1 to 4 carbon atoms or acyl of 1 to 4 carbon atoms; $R^4$ is hydrogen or alkyl of 1 to 4 carbon atoms; $R^5$ is hydrogen or acyl of 1 to 4 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 4 carbon atoms or benzyl.

3. A compound according to claim 1 wherein $R^1$ is hydrogen or alkyl of 1 or 2 carbon atoms; $R^2$ is hydrogen, fluoro, chloro or bromo; $R^3$ is hydrogen or alkyl of 1 or 2 carbon atoms; $R^4$ is hydrogen or alkyl of 1 or 2 carbon atoms; $R^5$ is hydrogen or acyl of 1 or 2 carbon atoms; X is $CONH_2$, hydroxyalkyl of 1 or 2 carbon atoms or $COOR^6$ wherein $R^6$ is hydrogen or alkyl of 1 or 2 carbon atoms; and Y is $CONH_2$, hydroxyalkyl of 1 or 2 carbon atoms or $COOR^7$ wherein $R^7$ is hydrogen or alkyl of 1 or 2 carbon atoms.

4. A compound according to claim 1 in the form of a pharmaceutically acceptable salt.

5. A compound according to claim 1 of the formula (II):

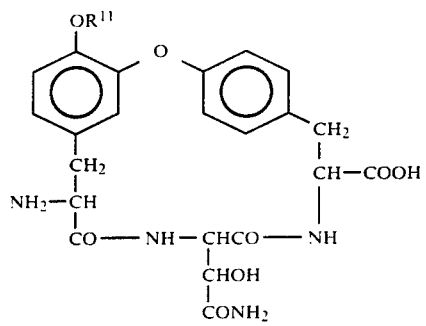

wherein $R^{11}$ is hydrogen or methyl.

6. The compound according to claim 1 which is:

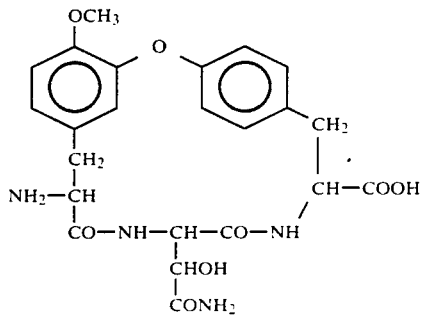

7. The compound according to claim 1 which is:

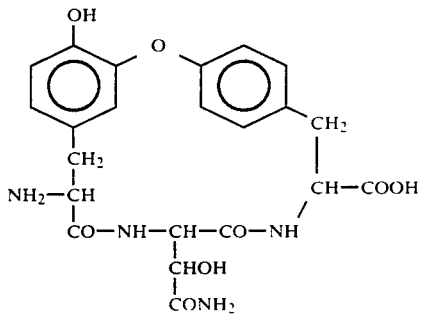

8. A pharmaceutical composition useful for inhibiting activity against amino-peptidase, immunomodulating action against living organisms and for the treatment of inflammation in humans and animals which comprises a therapeutically effective amount of a compound of the formula (I):

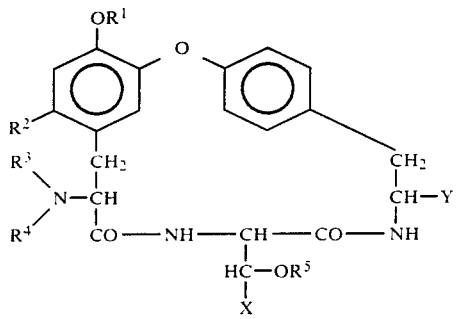

or a pharmaceutically acceptable salt thereof wherein $R^1$ is hydrogen, alkyl of 1 to 10 carbon atoms or acyl of 1 to 6 carbon atoms; $R^2$ is hydrogen or halo; $R^3$ is hydrogen, alkyl of 1 to 6 carbon atoms or acyl of 1 to 6 carbon atoms; $R^4$ is hydrogen or alkyl of 1 to 6 carbon atoms; $R^5$ is hydrogen or acyl of 1 to 6 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 10 carbon atoms or benzyl, in combination with a pharmaceutically acceptable carrier.

9. A composition according to claim 8 wherein $R^1$ is hydrogen, alkyl of 1 to 4 carbon atoms or acyl of 1 to 4 carbon atoms; $R^2$ is hydrogen, fluoro, chloro or bromo; $R^3$ is hydrogen, alkyl of 1 to 4 carbon atoms or acyl of 1 to 4 carbon atoms; $R^4$ is hydrogen or alkyl of 1 to 4 carbon atoms; $R^5$ is hydrogen or acyl of 1 to 4 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 4 carbon atoms or benzyl.

10. A composition according to claim 8 wherein $R^1$ is hydrogen or alkyl of 1 or 2 carbon atoms; $R^2$ is hydrogen, fluoro, chloro or bromo; $R^3$ is hydrogen or alkyl of 1 or 2 carbon atoms; $R^4$ is hydrogen or alkyl of 1 or 2 carbon atoms; $R^5$ is hydrogen or acyl of 1 or 2 carbon atoms; X is $CONH_2$, hydroxyalkyl of 1 or 2 carbon atoms or $COOR^6$ wherein $R^6$ is hydrogen or alkyl of 1 or 2 carbon atoms; and Y is $CONH_2$, hydroxyalkyl of 1 or 2 carbon atoms or $COOR^7$ wherein $R^7$ is hydrogen or alkyl of 1 or 2 carbon atoms.

11. A composition according to claim 8 wherein the compound is in the form of a pharmaceutically acceptable salt.

12. A composition according to claim 8 wherein the compound is of the formula (II):

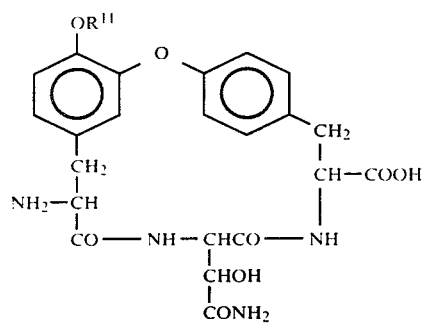

wherein $R^{11}$ is hydrogen or methyl.

13. A composition according to claim 8 wherein the compound is:

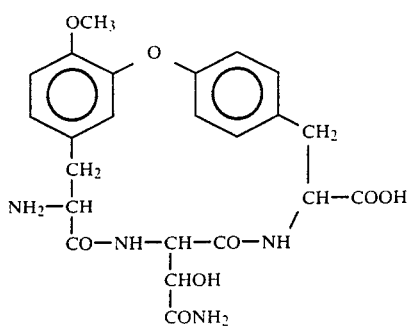
(III)

14. A composition according to claim 8 wherein the compound is:

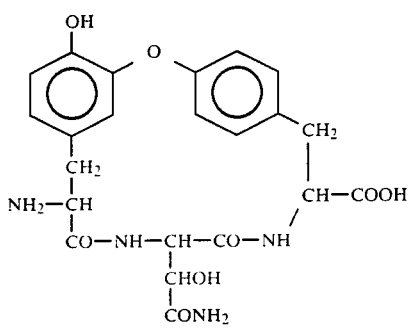
(IV)

15. A method of inhibiting activity against aminopeptidase, for effecting immunomodulating action against living organisms and for treating inflammation and inhibiting bradykinin formation in humans and animals which comprises administering to a human or animal in need thereof a therapeutically effective amount of a compound of the formula (I):

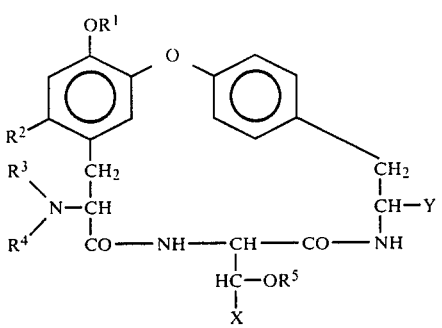
(I)

or a pharmaceutically acceptable salt thereof wherein $R^1$ is hydrogen, alkyl of 1 to 10 carbon atoms or acyl of 1 to 6 carbon atoms; $R^2$ is hydrogen or halo; $R^3$ is hydrogen, alkyl of 1 to 6 carbon atoms or acyl of 1 to 6 carbon atoms; $R^4$ is hydrogen or alkyl of 1 to 6 carbon atoms; $R^5$ is hydrogen or acyl of 1 to 6 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 10 carbon atoms or benzyl, in combination with a pharmaceutically acceptable carrier.

16. A method according to claim 15 wherein $R^1$ is hydrogen, alkyl of 1 to 4 carbon atoms or acyl of 1 to 4 carbon atoms; $R^2$ is hydrogen, fluoro, chloro or bromo; $R^3$ is hydrogen, alkyl of 1 to 4 carbon atoms or acyl of 1 to 4 carbon atoms; $R^4$ is hydrogen or alkyl of 1 to 4 carbon atoms; $R^5$ is hydrogen or acyl of 1 to 4 carbon atoms; X is $CONH_2$, hydroxyalkyl of 1 to 4 carbon atoms or $COOR^6$ wherein $R^6$ is hydrogen or alkyl of 1 to 4 carbon atoms; and Y is $CONH_2$, hydroxyalkyl of 1 to 4 carbon atoms or $COOR^7$ wherein $R^7$ is hydrogen, alkyl of 1 to 4 carbon atoms or benzyl.

17. A method according to claim 15 wherein $R^1$ is hydrogen or alkyl of 1 or 2 carbon atoms; $R^2$ is hydrogen, fluoro, chloro or bromo; $R^3$ is hydrogen or alkyl of 1 or 2 carbon atoms; $R^4$ is hydrogen or alkyl of 1 or 2 carbon atoms; $R^5$ is hydrogen or acyl of 1 or 2 carbon atoms; X is $CONH_2$, hydroxyalkyl of 1 or 2 carbon atoms or $COOR^6$ wherein $R^6$ is hydrogen or alkyl of 1 or 2 carbon atoms; and Y is $CONH_2$, hydroxyalkyl of 1 or 2 carbon atoms or $COOR^7$ wherein $R^7$ is hydrogen or alkyl of 1 or 2 carbon atoms.

18. A method according to claim 15 wherein the compound is in the form of a pharmaceutically acceptable salt.

19. A method according to claim 15 wherein the compound is of the formula (II):

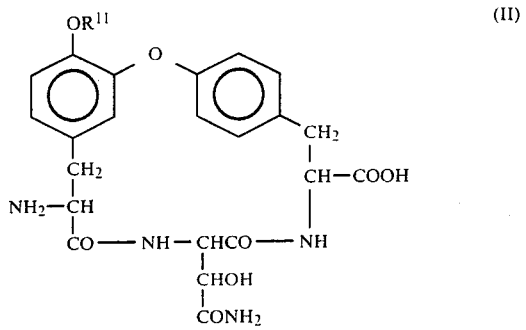
(II)

wherein $R^{11}$ is hydrogen or methyl.

20. A method according to claim 15 wherein the compound is:

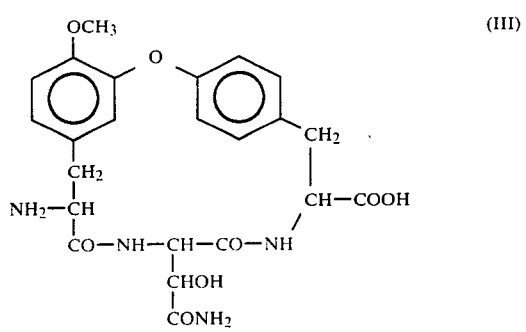
(III)

21. A method according to claim 15 wherein the compound is:

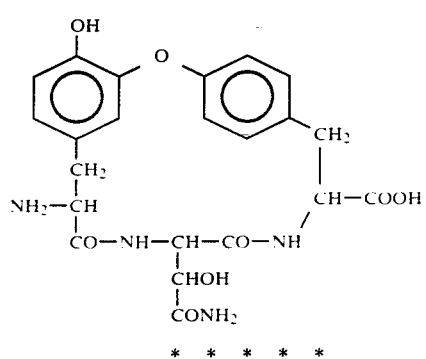
(IV)
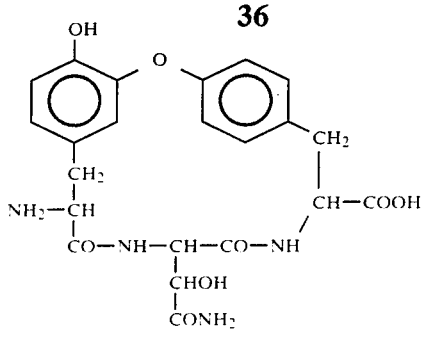
(IV)